Figure 1:
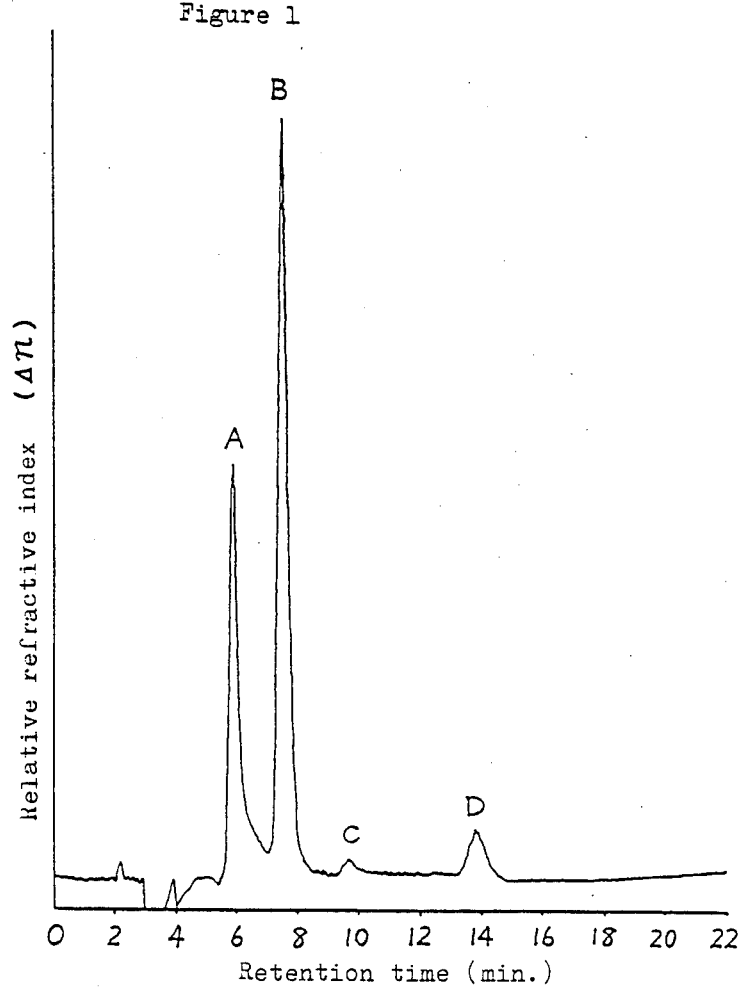

United States Patent [19]

Tsuji et al.

[11] 4,359,529
[45] Nov. 16, 1982

[54] MICROBIAL PROCESS FOR PRODUCING CHOLANIC ACID DERIVATIVES

[75] Inventors: Masao Tsuji; Yoshihiro Ichihara, both of Kurashiki, Japan

[73] Assignee: Kuraray Co., Ltd., Kurashiki, Japan

[21] Appl. No.: 173,815

[22] Filed: Jul. 30, 1980

[30] Foreign Application Priority Data

Aug. 21, 1979 [JP] Japan ............................... 54-106768
Aug. 31, 1979 [JP] Japan ............................... 54-112307
Sep. 27, 1979 [JP] Japan ............................... 54-124866
Jun. 19, 1980 [JP] Japan ............................... 55-83478

[51] Int. Cl.³ ................................................ C12P 33/00
[52] U.S. Cl. ................................... 435/52; 435/253; 435/830; 435/840; 435/843
[58] Field of Search .................................. 435/52, 253

[56] References Cited

U.S. PATENT DOCUMENTS 2,360,447 10/1944 Schmidt et al. ..................... 435/52

OTHER PUBLICATIONS

Lamanna et al., Basic Bacteriology, 3rd Ed. The Williams & Wilkins Co., 1965, pp. 721-726.
Metzler, Biochemistry, The Chemical Reactions of Living Cells, Academic Press Inc. pp. 945, 946 (1977).

*Primary Examiner*—Alvin E. Tanenholtz
*Attorney, Agent, or Firm*—Stevens, Davis, Miller & Mosher

[57] ABSTRACT

A microbial process for producing a cholanic acid derivative of the formula:

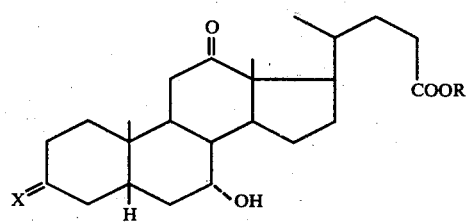

wherein X is

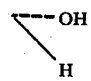

or =O; and R is hydrogen, an alkali metal or an alkaline earth metal, which comprises cultivating a microbe which is capable of growing in a medium containing cholic acid or a salt thereof as a substrate to produce the cholanic acid derivative, selected from the genera Arthrobacter, Brevibacterium and Corynebacterium, in a culture medium containing the substrate and collecting the resulting derivative.

10 Claims, 15 Drawing Figures

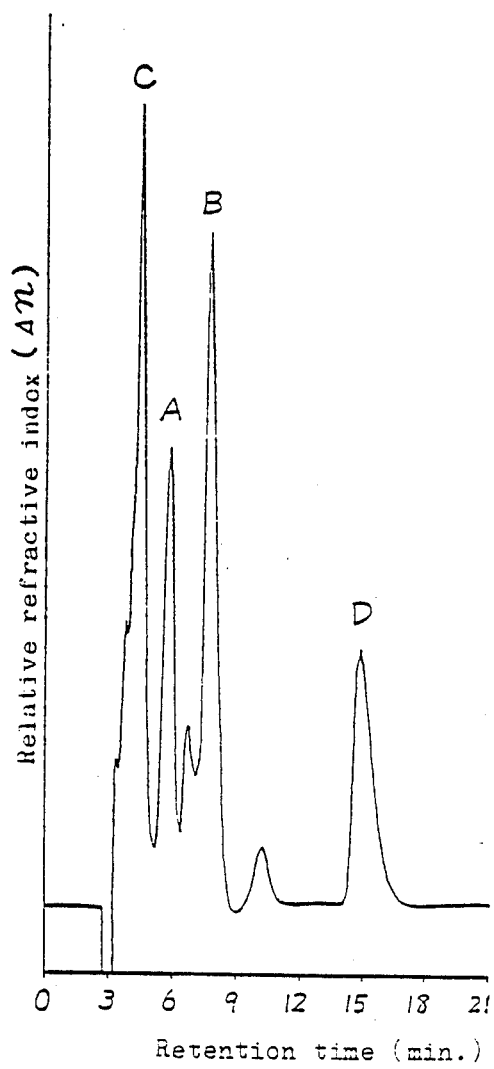

MICROBIAL PROCESS FOR PRODUCING CHOLANIC ACID DERIVATIVES

The present invention relates to a microbial process for producing a cholanic acid derivative of the formula:

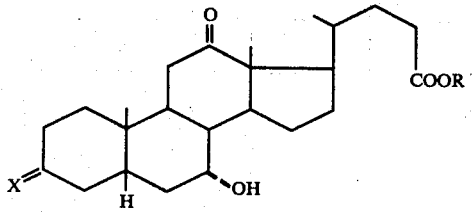

wherein X is

or =O; and R is hydrogen, an alkali metal or an alkaline earth metal and to microbes used in the process. More particularly, according to the present invention, the cholanic acid derivatives of the formula (I) can be produced in a high yield within a short period by cultivating a specific microbe in a culture medium containing cholic acid or a salt thereof as a substrate.

The cholanic acid derivative of the formula (I) wherein X is

namely, 3α,7α-dihydroxy-12-keto-5β-cholanic acid or a salt thereof is a useful intermediate for producing a gallstones solubilizer, chenodeoxycholic acid (CDCA). The cholanic acid derivative of the formula (I) wherein X is =O, namely, 7α-hydroxy-3,12-diketo-5β-cholanic acid or a salt thereof is a useful intermediate for producing deoxycholic acid which is a useful starting material in the production of progesterone and adrenal corticosteroid derivatives.

It has hitherto been known that the cholanic acid derivatives of the formula (I) can be obtained by a microbial process using cholic acid or a salt thereof as a substrate. For example, Hayakawa et al. disclose a process for producing 3α,7α-dihydroxy-12-keto-5β-cholanic acid by using *Streptomyces gelaticus* 1164 strain [The Journal of Biochemistry (Japan), Vol. 44, No. 2, pages 109 to 113 (1957); and Proceedings of Japan Academy, Vol. 32, pages 519 to 522 (1956)]. Hasegawa et al. disclose a process for producing 3α,7α-dihydroxy-12-keto-5β-cholanic acid by using *Aspergillus cinnamomeus* HUT 2026 strain [Hiroshima Journal of Medical Science, Vol. 8, No. 3, pages 277 to 283 (1959)]. Kikuchi et al. also disclose a process for producing 3α,7α-dihydroxy-12-keto-5β-cholanic acid by using *Staphylococcus epidermidis* H-1 strain [Journal of Biochemistry, Vol. 72, No. 1, pages 165 to 172 (1972)]. Further, Hayakawa et al. disclose a process for producing 7α-hydroxy-3,12-diketo-5β-cholanic acid by using *Streptomyces gelaticus* 1164 strain [Proceedings of Japan Academy, Vol. 32, pages 519 to 522 (1956)].

However, in these processes, a concentration of cholic acid as a substrate in a culture medium is low, such as not more than 10 g/l. According to the present inventors' experiment, it is necessitated to use cholic acid in a low concentration in the production of the cholanic acid derivatives by the known microbial processes since the microbes to be used are undergrown or hardly grow when a concentration of cholic acid in a culture medium is as high as not less than 20 g/l. Moreover, these known processes require too much period of time for the cultivation. Therefore, it has been desired to develop a process for producing the cholanic acid derivatives in a high yield within a short period of time. It has now been found that certain microbes belonging to the genera Arthrobacter, Brevibacterium and Corynebacterium can grow in a medium containing cholic acid or its salt as a substrate in a concentration ranging widely and can produce the cholanic acid derivatives in a high yield within a short period of time.

One object of the present invention is to provide a microbial process for producing the cholanic acid derivatives of the formula (I) in a high yield within a short period of time. Another object of the present invention is to provide novel microbes which are capable of growing in a medium containing cholic acid or a salt thereof as a substrate. These objects as well as other objects and advantages of the present invention will become apparent to those skilled in the art from the following description.

According to the present invention, there is provided a microbial process for producing a cholanic acid derivative of the formula (I) which comprises cultivating a microbe which is capable of growing in a medium containing cholic acid or a salt thereof as a substrate to produce the cholanic acid derivative, selected from the genera Arthrobacter, Brevibacterium and Corynebacterium, in a culture medium containing the substrate and collecting the resulting derivative.

Microbes to be used in the present invention are those isolated from soil and mutants thereof obtained by natural mutation, or produced by, for example, X-ray irradiation, ultraviolet irradiation, a mutating agent such as N-methyl-N'-nitro-N-nitroso guanidine, 4-nitroquinoline-N-oxide, acriflavine or ethylmethane sulfonate or combination thereof and the like.

Among the microbes being capable of producing the cholanic acid derivative of the formula (I) in a culture medium containing cholic acid or its salt obtained by the present inventor, the representatives are deposited with Fermentation Research Institute, Agency of Industrial Science and Technology, Japan (hereinafter, referred to as FERM) and with American Type Culture Collection, U.S.A. (hereinafter, referred to as ATCC). They are Arthrobacter CA-35 strain (FERM-P No. 5145; ATCC No. 31651), Arthrobacter CA-35-A589-29-32 strain (FERM-P No. 5522; ATCC No. 31652), Arthrobacter CA-35-A589-47 strain (FERM-P No. 5523; ATCC No. 31653), Arthrobacter CA-35-A849 strain (FERM-P No. 5524; ATCC No. 31654), Arthrobacter CA-35-A-1071-15 strain (FERM-P No. 5525; ATCC No. 31655), Arthrobacter CA-35-A-1448 strain (FERM-P No. 5526; ATCC No. 31656), Arthrobacter CA-35-A-1475 strain (FERM-P No. 5527; ATCC No. 31657), Arthrobacter CA-35-A-1766-15 strain (FERM-P No. 5528; ATCC No. 31658), Arthrobacter CA-35-M-965-3 strain (FERM-P No. 5529; ATCC No. 31659), Arthrobacter CA-35-Y-37-12 strain (FERM-P No. 5530; ATCC No. 31660), Brevibacterium CA-6 strain (FERM-P No. 5144; ATCC No. 31661) and Corynebacterium CA-53 strain (FERM-P No. 5532; ATCC No. 31662). Arthrobacter CA-35, Brevibacterium CA-6 and Corynebacterium CA-53 strains are wild type strains and the other nine Arthrobacter strains are mutants of Arthrobacter CA-35 strain. Arthrobacter CA-35-Y-37-12 strain is produced by ultraviolet irradiation. The other eight mutants of Arthrobacter CA-35 strain are obtained by treatment of the parent strain with N-methyl-N'-nitro-N-nitrosoguanidine.

The morphological, cultural and physiological characteristics of these strains are set forth in Table 1. For comparison, these characteristics of Arthrobacter simplex IAM 1660 strain which has a relation to Arthrobacter CA-35 strain are also shown in Table 1.

TABLE 1

| Characteristics | *Arthrobacter simplex* IAM 1660 strain | Arthrobacter CA-35 strain |
|---|---|---|
| Microscopic observation | | |
| Form | rods (sometimes swollen or curved) | rods (sometimes snapped or curved) |
| Division | — | snapping |
| Size ($\mu$) | 0.4–0.5 × 1–3 | 0.8–0.9 × 1.7–2.2 |
| Flagellum | none | none |
| Spore | none | none |
| Gram stain | positive-variable | positive |
| Acid fast stain | none | none |
| Cultural observation | | |
| Bouillon agar plate | circular, slightly raised, colorless, smooth, glistening, transparent | circular, slightly raised, yellow to cream-colored, smooth, glistening opaque |
| Gelatin stab | saccate liquefaction | no liquefaction |
| Litmus milk | litmus reduced, milk cleared | litmus reduced, milk unchanged |
| BCP milk | clearing, becoming alkaline | alkaline, not coagulated and not peptonized |
| Physiological character[1] | | |
| Nitrate reduction | + | + |
| Denitrification | — | — |
| Methyl red test | — | — |
| Voges-Proskauer test | — | — |
| Indole production | — | — |
| H$_2$S production | + | + |
| Starch hydrolysis | — | — |
| Citrate utilization | + | + |
| Assimilation of inorganic nitrogen sources | + | + |
| Urease | — | — |
| Oxidase | — | ± to — |
| Catalase | + | + |
| Require of oxygen | aerobic | aerobic |
| Oxidation/Fermentation test | — | oxidative |

| Production of acids and[2] gases from carbohydrates | growth | acids | gases | assimilation | growth | acids | gases | assimilation |
|---|---|---|---|---|---|---|---|---|
| 1. L-arabinose | + | — | — | — | ± | — | — | +++ |
| 2. D-xylose | + | — | — | — | + | — | — | ± to — |
| 3. D-glucose | + | — | — | ++ | + | + | — | +++ |
| 4. D-mannose | + | — | — | — | + | — | — | ++ |
| 5. D-fructose | + | — | — | + | + | + | — | +++ |
| 6. D-galactose | + | — | — | — | + | — | — | +++ |
| 7. Maltose | + | — | — | + | + | — | — | +++ |
| 8. Sucrose | + | — | — | ± | + | — | — | ± |
| 9. Lactose | + | — | — | — | + | — | — | — |
| 10. Trehalose | + | — | — | + | + | — | — | — |
| 11. D-sorbitol | + | — | — | — | + | — | — | — |
| 12. D-mannitol | + | — | — | — | + | — | — | — |
| 13. Inositol | + | — | — | — | + | — | — | — |
| 14. Glycerol | + | — | — | — | + | — | — | +++ |
| 15. Starch | + | — | — | — | + | + | — | — |

| Characteristics | Arthrobacter CA-35-A589-29-32 strain | Arthrobacter CA-35-A589-47 strain |
|---|---|---|
| Microscopic observation | | |
| Form | short rod | short rod |
| Division | — | — |
| Size ($\mu$) | 0.8–1.0 × 1.3–2.0 | 0.8–1.0 × 1.3–2.3 |
| Flagellum | polar flagellum | flagellum |
| Spore | none | none |
| Gram stain | positive | positive |
| Acid fast stain | none | none |
| Cultural observation | | |
| Bouillon agar plate | circular, flat, yellow, smooth, glistening, opaque | circular, flat, yellow, smooth, glistening, opaque |
| Bouillon agar plate containing cholic acid (10 g/l) | circular, flat, yellow, smooth, glistening, opaque | circular, flat, white to pale cream-colored, smooth, glistening, opaque |
| Gelatin stab | liquefaction | liquefaction |
| Litmus milk | litmus reduced, milk not | litmus reduced, milk not |

TABLE 1-continued

| | Arthrobacter CA-35-A 849 strain | | Arthrobacter CA-35-A-1071-15 strain | |
|---|---|---|---|---|
| BCP milk | coagulated and not peptonized alkaline, not coagulated and not peptonized | | coagulated and not peptonized alkaline, not coagulated and not peptonized | |
| Physiological character[1] | | | | |
| Nitrate reduction | + | | + | |
| Denitrification | − | | − | |
| Methyl red test | − | | − | |
| Voges-Proskauer test | − | | − | |
| Indole production | − | | − | |
| H$_2$S production | + | | + | |
| Starch hydrolysis | − | | − | |
| Citrate utilization | + | | + | |
| Assimilation of inorganic nitrogen sources | | | | |
|    ammonium | + | | + | |
|    nitrate | + | | + | |
| Urease | − | | − | |
| Oxidase | − | | − | |
| Catalase | + | | + | |
| Require of oxygen | aerobic | | aerobic | |
| Oxidation/Fermentation test | oxidative | | − | |
| Production of acids and[2] gases from carbohydrates | acids | gases | acids | gases |
| 1. L-arabinose | + | − | + | − |
| 2. D-xylose | − | − | − | − |
| 3. D-glucose | + | − | − | − |
| 4. D-mannose | − | − | − | − |
| 5. D-fructose | + | − | + | − |
| 6. D-galactose | − | − | − | − |
| 7. Maltose | + | − | + | − |
| 8. Sucrose | − | − | − | − |
| 9. Lactose | − | − | − | − |
| 10. Trehalose | − | − | − | − |
| 11. D-sorbitol | − | − | − | − |
| 12. D-mannitol | − | − | − | − |
| 13. Inositol | − | − | − | − |
| 14. Glycerol | − | − | − | − |
| 15. Starch | − | − | − | − |

| Characteristics | Arthrobacter CA-35-A 849 strain | Arthrobacter CA-35-A-1071-15 strain |
|---|---|---|
| Microscopic observation | | |
| Form | short rod | short rod |
| Division | − | − |
| Size (μ) | 0.7–1.0 × 1.3–2.3 | 0.8–1.0 × 1.3–2.5 |
| Flagellum | none | none |
| Spore | none | none |
| Gram stain | positive | positive |
| Acid fast stain | none | none |
| Cultural observation | | |
| Bouillon agar plate | circular, flat, yellow, smooth, glistening, opaque | circular, flat, yellow, smooth, glistening, opaque |
| Bouillon agar plate containing cholic acid (10 g/l) | circular, flat, white to pale cream-colored, smooth, glistening, opaque | circular, flat, white to pale cream-colored, smooth, glistening, opaque |
| Gelatin stab | liquefaction | liquefaction |
| Litmus milk | litmus reduced, milk not coagulated and not peptonized | litmus reduced, milk not coagulated and not peptonized |
| BCP milk | alkaline, not coagulated and not peptonized | alkaline, not coagulated and not peptonized |
| Physiological character[1] | | |
| Nitrate reduction | + | + |
| Denitrification | − | − |
| Methyl red test | − | − |
| Voges-Proskauer test | − | − |
| Indole production | − | − |
| H$_2$S production | + | + |
| Starch hydrolysis | − | − |
| Citrate utilization | + | + |
| Assimilation of inorganic nitrogen sources | | |
|    ammonium | + | + |
|    nitrate | + | + |
| Urease | − | − |
| Oxidase | − | − |
| Catalase | + | + |
| Require of oxygen | aerobic | aerobic |
| Oxidation/Fermentation test | oxidative | oxidative |
| Production of acids and[2] | | |

TABLE 1-continued

| gases from carbohydrates | acids | gases | acids | gases |
|---|---|---|---|---|
| 1. L-arabinose | − | − | + | − |
| 2. D-xylose | − | − | − | − |
| 3. D-glucose | + | − | + | − |
| 4. D-mannose | − | − | + | − |
| 5. D-fructose | + | − | + | − |
| 6. D-galactose | − | − | + | − |
| 7. Maltose | + | − | + | − |
| 8. Sucrose | − | − | − | − |
| 9. Lactose | − | − | − | − |
| 10. Trehalose | − | − | − | − |
| 11. D-sorbitol | − | − | − | − |
| 12. D-mannitol | − | − | − | − |
| 13. Inositol | − | − | − | − |
| 14. Glycerol | + | − | + | − |
| 15. Starch | − | − | − | − |

| Characteristics | Arthrobacter CA-35-A-1448 strain | Arthrobacter CA-35-A-1475 strain |
|---|---|---|
| Microscopic observation | | |
| Form | short rod | short rod to coccus |
| Division | — | — |
| Size (μ) | 0.7–1.0 × 1.2–2.0 | 1.0–1.3 × 1.2–1.8 |
| Flagellum | flagellum | flagellum |
| Spore | none | none |
| Gram stain | positive | positive |
| Acid fast stain | none | none |
| Cultural observation | | |
| Bouillon agar plate | circular, flat, yellow, smooth, glistening, opaque | circular, flat, yellow, smooth, glistening, opaque |
| Bouillon agar plate containing cholic acid (10 g/l) | circular, flat, white to pale cream-colored, smooth, glistening, opaque | circular, flat, white to pale cream-colored, smooth, glistening, opaque |
| Gelatin stab | liquefaction | liquefaction |
| Litmus milk | litmus reduced, milk not coagulated and not peptonized | litmus reduced, milk not coagulated and not peptonized |
| BCP milk | alkaline, not coagulated and not peptonized | alkaline, not coagulated and not peptonized |
| Physiological character[1] | | |
| Nitrate reduction | + | + |
| Denitrification | − | − |
| Methyl red test | − | − |
| Voges-Proskauer test | − | − |
| Indole production | − | − |
| H$_2$S production | + | + |
| Starch hydrolysis | − | − |
| Citrate utilization | + | + |
| Assimilation of inorganic nitrogen sources | | |
| ammonium | + | + |
| nitrate | + | + |
| Urease | − | − |
| Oxidase | − | − |
| Catalase | + | − |
| Require of oxygen | aerobic | aerobic |
| Oxidation/Fermentation test | oxidative | — |

| Production of acids and[2] gases from carbohydrate | acids | gases | acids | gases |
|---|---|---|---|---|
| 1. L-arabinose | + | − | − | − |
| 2. D-xylose | − | − | − | − |
| 3. D-glucose | + | − | − | − |
| 4. D-mannose | − | − | − | − |
| 5. D-fructose | + | − | + | − |
| 6. D-galactose | − | − | − | − |
| 7. Maltose | + | − | − | − |
| 8. Sucrose | − | − | − | − |
| 9. Lactose | − | − | − | − |
| 10. Trehalose | − | − | − | − |
| 11. D-sorbitol | − | − | − | − |
| 12. D-mannitol | − | − | − | − |
| 13. Inositol | − | − | − | − |
| 14. Glycerol | + | − | − | − |
| 15. Starch | − | − | − | − |

| Characteristics | Arthrobacter CA-35-A-1766-15 strain | Arthrobacter CA-35-M-965-3 strain |
|---|---|---|
| Microscopic observation | | |
| Form | short rod | short rod to coccus |
| Division | — | — |
| Size (μ) | 0.6–1.2 × 1.0–2.3 | 1.0–1.2 × 0.8–1.6 |

TABLE 1-continued

| | | |
|---|---|---|
| Flagellum | flagellum | flagellum |
| Spore | none | none |
| Gram stain | positive | positive |
| Acid fast stain | none | none |
| Cultural observation | | |
| Bouillon agar plate containing cholic acid (10 g/l) | circular, flat, yellow, smooth, glistening, opaque | circular, flat, yellow, smooth, colored, smooth, glistening, opaque |
| Gelatin stab | liquefaction | no liquefaction |
| Litmus milk | litmus reduced, milk not coagulated and not peptonized | litmus reduced, milk not coagulated and not peptonized |
| BCP milk | not peptonized | no peptonized |
| Physiological character[1] | | |
| Nitrate reduction | + | + |
| Denitrification | − | − |
| Methyl red test | − | − |
| Voges-Proskauer test | − | − |
| Indole production | − | − |
| $H_2S$ production | + | + |
| Starch hydrolysis | − | − |
| Citrate utilization | + | + |
| Assimilation of inorganic nitrogen sources | | |
|   ammonium | + | + |
|   nitrate | − | + |
| Urease | − | − |
| Oxidase | − | − |
| Catalase | + | + |
| Require of oxygen | aerobic | aerobic |
| Oxidation/Fermentation test | oxidative | oxidative |

| Production of acids and[2] gases from carbohydrates | acids | gases | acids | gases |
|---|---|---|---|---|
| 1. L-arabinose | − | − | + | − |
| 2. D-xylose | − | − | − | − |
| 3. D-glucose | + | − | + | − |
| 4. D-mannose | − | − | − | − |
| 5. D-fructose | + | − | + | − |
| 6. D-galactose | − | − | − | − |
| 7. Maltose | + | − | + | − |
| 8. Sucrose | − | − | − | − |
| 9. Lactose | − | − | − | − |
| 10. Trehalose | − | − | − | − |
| 11. D-sorbitol | − | − | − | − |
| 13. Inositol | − | − | − | − |
| 14. Glycerol | + | − | − | − |
| 15. Starch | − | − | − | − |

| Characteristics | Arthrobacter CA-35-Y-37-12 strain | Brevibacterium CA-6 strain |
|---|---|---|
| Microscopic observation | | |
| Form | short rod | rod |
| Division | − | − |
| Size ($\mu$) | 0.8–1.0 × 1.5–2.5 | 1.0 × 2.5–4.0 |
| Flagellum | flagellum | polar Flagellum |
| Spore | none | none |
| Gram stain | positive | positive |
| Acid fast stain | none | none |
| Cultural observation | | |
| Bouillon agar plate | circular, flat, yellow, smooth, glistening, opaque | undulate, slightly raised, colorless, smooth, glistening, translucent |
| Bouillon agar plate containing cholic acid (10 g/l) | circular, flat, cream-colored, smooth, glistening, opaque | — |
| Gelatin stab | liquefaction | liquefaction |
| Litmus milk | litmus reduced, milk not coagulated and not peptonized | peptonized and becoming alkaline |
| BCP milk | alkaline, not coagulated and not peptonized | peptonized and becoming alkaline |
| Physiological character[1] | | |
| Nitrate reduction | + | − |
| Denitrification | − | + |
| Methyl red test | − | − |
| Voges-Proskauer test | − | − |
| Indole production | − | − |
| $H_2S$ production | + | + |
| Starch hydrolysis | − | + |
| Citrate utilization | + | + |
| Assimilation of inorganic nitrogen sources | | |
|   ammonium | + | |

TABLE 1-continued

| | | | | | | |
|---|---|---|---|---|---|---|
| nitrate | + | | | | | |
| Urease | − | | | − | | |
| Oxidase | − | | | ± | | |
| Catalase | + | | | + | | |
| Require of oxygen | aerobic | | | aerobic | | |
| Oxidation/Fermentation test | oxidative | | | − | | |
| Production of acids and[2] gases from carbohydrates | acids | gases | growth | acids | gases | assimilation |
| 1. L-arabinose | + | − | + | + | − | +++ |
| 2. D-xylose | − | − | + | + | − | ± |
| 3. D-glucose | + | − | + | + | − | +++ |
| 4. D-mannose | − | − | + | + | − | + |
| 5. D-fructose | + | − | + | + | − | +++ |
| 6. D-galactose | − | − | + | ± | − | +++ |
| 7. Maltose | + | − | + | − | − | +++ |
| 8. Sucrose | − | − | + | − | − | − |
| 9. Lactose | − | − | + | − | − | − |
| 10. Trehalose | − | − | + | − | − | ± |
| 11. D-sorbitol | − | − | + | − | − | − |
| 12. D-mannitol | − | − | + | − | − | − |
| 13. Inositol | + | − | + | − | − | +++ |
| 14. Glycerol | + | − | + | + | − | +++ |
| 15. Starch | − | − | + | − | − | − |

| Characteristics | Corynebacterium CA-53 strain | |
|---|---|---|
| Microscopic observation | | |
| Form | rod, coryneform | |
| Division | snapping | |
| Size (μ) | 1.3–2.4 × 1.0–1.2 | |
| Flagellum | none | |
| Spore | none | |
| Gram stain | positive | |
| Acid fast stain | none | |
| Cultural observation | | |
| Nutrient agar plate | circular, flat, yellow, smooth, glistening, opaque | |
| Gelatin stab | no liquefaction | |
| Litmus milk | litmus reduced with brown sediment | |
| BCP milk | akaline | |
| Physiological character[1] | | |
| Nitrate reduction | + | |
| Denitrification | − | |
| Methyl red test | − | |
| Voges-Proskauer test | − | |
| Indole production | − | |
| H$_2$S production | + | |
| Starch hydrolysis | − | |
| Citrate utilization | + | |
| Assimilation of inorganic nitrogen sources | + | |
| Urease | − | |
| Oxidase | + | |
| Catalase | + | |
| Require of oxygen | aerobic | |
| Oxidation/Fermentation test | − | |
| Production of acids and[2] gases from carbohydrates | acids | gases |
| 1. L-arabinose | − | − |
| 2. D-xylose | − | − |
| 3. D-glucose | − | − |
| 4. D-mannose | − | − |
| 5. D-fructose | − | − |
| 6. D-galactose | − | − |
| 7. Maltose | − | − |
| 8. Sucrose | − | − |
| 9. Lactose | − | − |
| 10. Trehalose | − | − |
| 11. D-sorbitol | − | − |
| 12. D-mannitol | − | − |
| 13. Inositol | − | − |
| 14. Glycerol | − | − |

TABLE 1-continued

| | 15. Starch | — | — |

Remarks:
(1)The symbols used in Physiological character mean as follows:
+: The strain has the corresponding character or produces the corresponding product.
±: It is difficult to determine whether the strain has the corresponding character or produces the corresponding product or not.
−: The strain does not have the corresponding character or does not produce the corresponding product.
(2)The symbols used in Production of acids and gases from carbohydrates mean as follows:
(i) growth, acids and gases: The strain was cultivated in Hugh and Leifson medium provided that each of the carbohydrates 1 to 15 is substituted for the carbon source and the growth thereof and acids and gases production were observed.
+: The strain grows or a acid or a gas is produced.
±: It is difficult to determine whether the strain grows or a acid or a gas is produced or not.
−: The strain does not grow or a acid or gas in not produced.
(ii) assimilation:
The culture medium comprising $NH_4NO_3$ (2 g/l), $KH_2PO_4$ (2 g/l), $K_2HPO_4$ (5 g/l), $MgSO_4 \cdot 7H_2O$ (0.2 g/l), yeast extract (0.1 g/l) and one of the carbohydrates 1 to 15 (5 g/l) was put into a tube (diameter 21 mm), the strain was cultivated with shaking therein and its assimilation (growth) was observed.
−: The strain does not grow.
±: The strain grows slightly.
+: The strain grows.
++: The strain grows well
+++: The strain grows very well.

On the basis of these morphological, cultural and physiological characteristics, the classification of the strains has been determined according to Bergey's Mannual of Determinative Bacteriology 7th and 8th Editions.

It is determined that Arthrobacter CA-35 strain has a relation to *Arthrobacter simplex* in view of its microscopic observation such as form, gram stain and the like as well as its physiological character. However, Arthrobacter CA-35 strain is different from *Arthrobacter simplex* IAM 1660 strain in view of their pigment production, assimilation of carbohydrates and growth in a medium containing cholic acid. Arthrobacter CA-35 strain can grow in a medium containing sodium cholate as the sole carbon source in a high concentration such as about 20 to 500 g/l to produce as main metabolic products 7α-hydroxy-3,12-diketo-5β-cholanic acid, 3α,7α-dihydroxy-12-keto-5β-cholanic acid, 7α,12α-dihydroxy-3-keto-5β-cholanic acid and/or sodium salts thereof whereas *Arthrobacter simplex* IAM 1660 strain can hardly grow in a medium containing sodium cholate as the sole carbon source in a concentration of 10 g/l.

Arthrobacter CA-35 strain produces yellow to cream-colored pigments. On the other hand, as a microbe which belongs to the genus Arthrobacter and has a pigment productivity, there exist *Arthrobacter oxydans, Arthrobacter aurescens* and *Arthrobacter ureafaciens*. However, Arthrobacter CA-35 strain is also different from these microbes since *Arthrobacter oxydans* and *Arthrobacter aurescens* are usually gram-negative and hydrolyze starch and *Arthrobacter ureafaciens* is usually gram-negative and does not reduce a nitrate. Thus, it is believed that Arthrobacter CA-35 strain constitutes a new species belonging to the genus Arthrobacter since it is different from strains of standard species belonging to the genus Arthrobacter.

Although some of the mutants of Arthrobacter CA-35 strain are quite different from the parent strain in view of flagella, it is determined that these mutants belong to Arthrobacter since, generally, a mutant is classified into the same species of its parent strain.

It is determined that Brevibacterium CA-6 strain belongs to the genus Brevibacterium in view of its microscopic observation such as gram stain and the like and its physiological character. However, Brevibacterium CA-6 strain is somewhat different from other microbes belonging to the genus Brevibacterium since the other microbes have peritrichous flagella whereas Brevibacterium CA-6 strain has polar flagellum and so on.

Further, it is determined that Corynebacterium CA-53 strain has a close relation to *Corynebacterium equi*.

The process of the present invention is carried out by cultivating a microbe which is capable of growing in a medium containing cholic acid or its salt as a substrate, selected from the genera Arthrobacter, Brevibacterium and Corynebacterium, like the above in a culture medium containing cholic acid or its salt as a substrate.

In the present invention, cholic acid per se can be used as a substrate. There can be also used an alkali metal salt of cholic acid such as sodium cholate, potassium cholate or the like or an alkaline earth metal salt of cholic acid such as calcium cholate, magnesium cholate or the like, preferably an alkali metal salt. When a cholate is used, it is dissolved in a water to prepare an aqueous solution containing the cholate in a predetermined concentration. Alternatively, a certain amount of an alkali metal compound or an alkaline earth metal compound which forms a salt with cholic acid may previously be dissolved in water and added thereto cholic acid to obtain an aqueous solution containing a cholate in a pre-determined concentration. Concentration of cholic acid or its salt may be varied widely in a range of from about 1 to 500 g/l as cholic acid. In view of a yield of the desired cholanic acid derivatives of the formula (I), conditions for cultivation and economic efficiency such as operability, workability and the like, it is recommended that cholic acid or its salt is used in a concentration of about 5 to 300 g/l, preferably, about 10 to 200 g/l as cholic acid.

Cultivation can be carried out according to a known method and, usually, a shaking or submerged culture using a liquid medium is employed.

As a medium, there can be used one containing nutrients which can be assimilated by a microbe to be used. A medium can contain cholic acid or its salt as the sole carbon source or an additional carbon source such as a pentose (e.g. arabinose etc.), a hexose (e.g. glucose, mannose, fructose, galactose etc.), a disaccharide (e.g. maltose etc.), a starch decomposition product (e.g. dextrin etc.), a sugar alcohol (e.g. sorbitol etc.), a polyvalent alcohol (e.g. glycerol etc.), a mixture thereof or the like and/or another nutrient such as a polypeptone, a peptone, meat extract, malt extract, corn steep liquor, yeast extract, an amino acid, a mixture thereof or the like. Usually, an additional carbon source and/or another nutrient can be added to a medium in a concentration of about 0.1 to 10 g/l. As a nitrogen source, there can be used, for example, ammonium sulfate, ammonium chloride, ammonium phosphate, ammonium nitrate, sodium nitrate, potassium nitrate, a mixture thereof and the like. Usually, a nitrogen source can be added to a medium in a concentration of about 0.5 to 5 g/l. Further, as inorganic salts, dipotassium hydrogen phosphate, potassium dihydrogen phosphate, magnesium sulfate and the like can be added to a medium, usually, in a concentration of about 0.1 to 10 g/l. Cultivation can be carried out in a shaking or submerged culture at 25° to 35° C. for 6 hours to 5 days.

According to the process of the present invention, cholic acid or its salt used as a substrate is converted into the cholanic acid derivatives of the formula (I) and a small amount of 7α,12α-dihydroxy-3-keto-5β-cholanic acid or its salt when Arthrobacter CA-35 strain is used. It has been found that the cholanic acid derivative of the formula (I) wherein X is

namely, 3α,7α-dihydroxy-12-keto-5β-cholanic acid or its salt is predominantly produced when the above mutants of Arthrobacter CA-35 are used. Therefore, when 3α,7α-dihydroxy-12-keto-5β-cholanic acid or its salt is desired, it is preferable to use these mutants, especially, Arthrobacter CA-35-A589-29-32 strain (FERM-P No. 5522; ATCC No. 31652), Arthrobacter CA-35-A589-47 strain (FERM-P No. 5523; ATCC No. 31653), and Arthrobacter CA-35-A-1766-15 strain (FERM-P No. 5528; ATCC No. 31658). Particularly, Arthrobacter CA-35-A-589-29-32 strain and Arthrobacter CA-35-A589-47 strain are more preferable. When Brevibacterium CA-6 strain is used, cholic acid or its salt is converted into the cholanic acid derivatives of the formula (I) and a small amount of 7α-hydroxy-3,12-diketo-Δ⁴-cholenic acid or its salt. When Corynebacterium CA-53 strain is used, cholic acid or its salt is converted into the cholanic acid derivatives of the formula (I) and 7α-hydroxy-3,12-diketo-Δ⁴-cholenic acid or its salt.

After completion of cultivation, products accumulated in the medium are separated from the medium and purified. Firstly, insoluble materials in the medium such as microbial cells and the like are removed from the medium by a known method such as filtration, centrifugation and the like. Then, a filtrate or supernatant is acidified by addition of an acid such as hydrochloric acid to precipitate products therein. At the same time, cholic acid or its salt used as a substrate which remains without being converted is also precipitated as cholic acid. After separation of the resulting precipitate, the filtrate or supernatant is further extracted with an inert organic solvent such as ethyl acetate, or the like and the solvent is distilled off from the extract to obtain a residue. Thereby, remaining products and the substrate are almost completely recovered. The resulting residue is combined with the above obtained precipitate.

A mixture of products and cholic acid thus obtained is subjected to chromatography to isolate the desired product. For example, products obtained by using Arthrobacter CA-35 strain or a mutant thereof can be isolated as follows: Products and cholic acid are converted into methyl esters thereof and the obtained methyl esters are subjected to chromatography on a silica gel column by successively eluting with chloroform, chloroformethanol (99:1, v/v) and then chloroform-ethanol (97:3, v/v). The desired 7α-hydroxy-3,12-diketo-5β-cholanic acid methyl ester is eluted with chloroform. By elution with chloroform-ethanol (99:1, v/v), firstly, one of the by-products, 7α,12α-dihydroxy-3-keto-5β-cholanic acid methyl ester and then, the desired 3α,7α-dihydroxy-12-keto-5β-cholanic acid methyl ester are eluted. Methyl cholate is eluted with chloroform-ethanol (97:3, v/v). These methyl esters can be converted into the corresponding acids by hydrolysis according to a standard method. Alternatively, when Brevibacterium CA-6 strain or Corynebacterium CA-53 strain is used, products can be isolated, for example, as follows: A mixture of products and cholic acid are directly subjected to chromatography on a silica gel by succesively eluting with chloroform-ethanol (98:2, v/v) and then chloroform-ethanol (97:3, v/v). The desired 7α-hydroxy-3,12-diketo-5β-cholanic acid is eluted with chloroform-ethanol (98:2, v/v). By elution with chloroform-ethanol (97:3, v/v), firstly, a by-product, 7α-hydroxy-3,12-diketo-Δ⁴-cholenic acid is eluted and then, the desired 3α,7α-dihydroxy-12-keto-5β-cholanic acid is eluted.

3α,7α-dihydroxy-12-keto-5β-cholanic acid or its salt obtained by the present invention can be readily reduced according to Huang Minlon reduction method to give a useful gallstones solubilizer, chenodeoxycholic acid (CDCA).

7α-hydroxy-3,12-diketo-5β-cholanic acid or its salt can be readily converted into deoxycholic acid, which is a useful starting material in the production of progesterone and adrenal corticosteroid derivatives, by dehydration, followed by hydrogenation according to a standard method.

The following examples and reference examples further illustrate the present invention in detail but are not to be construed to limit the scope thereof.

Preparation of mutants

One loopful of Arthrobacter CA-35 strain (FERM-P No. 5145; ATCC No. 31651) cultivated on a slant medium (medium A; NaOH 0.5%, cholic acid 5.0%, peptone 0.5%, yeast extract 0.5%, NaCl 0.5% and agar 1.5%) was inoculated into a medium (10 ml, medium B: NaOH 1%, cholic acid 10%, NH₄NO₃ 0.2%, KH₂PO₄ 0.2%, K₂HPO₄ 0.5%, MgSO₄.7H₂O 0.02% and yeast extract 0.01%) in a test tube (200 mm × 21 mm in diameter), and incubated with shaking at 30° C. for 24 hours. The resulting culture (0.3 ml) was added to a medium (10 ml, medium C: NaOH 0.05%, cholic acid 0.5%, glucose 0.5%, NH₄NO₃ 0.2%, KH₂PO₄ 0.2%, K₂HPO₄ 0.5%, MgSO₄.7H₂O 0.02% and yeast extract 0.01%) in a test tube (200 mm × 21 mm in diameter) and incubated with shaking at 30° C. for 15 to 16 hours. The microbial cells in a log phase were harvested by a membrane filter (pore size 0.45μ) under aseptic conditions, washed with 0.1 M phosphate buffer (pH 7.0, 20 ml) and suspended in the same buffer (25 ml).

A treatment of mutation was carried out by adding N-methyl-N'-nitro-N-nitrosoguanidine in a final concentration of 50 μg/ml to the above cell suspension (4 ml) in a test tube (200 mm × 21 mm in diameter) and incubating the mixture with shaking at 30° C. for 45 minutes. Under this condition, a lethal rate of Arthrobacter CA-35 strain was about 80%.

The cells thus treated were harvested by a membrane filter (pore size, 0.45μ) under aseptic conditions, washed with 0.1 M phosphate buffer (pH 7.0, 20 ml) and suspended in the same buffer (25 ml). The resulting cell suspension was diluted with a sterilized normal saline solution and spreaded on agar plates (medium D: NaOH 0.1%, cholic acid 1.0%, $NH_4NO_3$ 0.2%, $KH_2PO_4$ 0.2%, $K_2HPO_4$ 0.5%, $MgSO_4.7H_2O$ 0.02%, yeast extract 0.01% and agar 1.5%) so as to form 300 to 500 colonies per one plate. The plates were incubated at 30° C. for 4 days. Each pin point colony thus formed was isolated and incubated on a plate (medium E: peptone 0.5%, yeast extract 0.5%, NaCl 0.5% and agar 1.5%) at 30° C. for 24 hours. Each colony formed on the plate of medium E was replicated on a plate of medium D and incubated at 30° C. for 20 hours.

Each colony on the above plate of medium E, of which replicated colony did not grow on the plate of medium D, was incubated on a slant medium (medium F: NaOH 0.1%, cholic acid 1.0%, peptone 0.5%, yeast extract 0.5%, NaCl 0.5% and agar 1.5%) at 30° C. for 24 hours. One loopful of this slant culture was inoculated into a medium (10 ml, medium G: NaOH 0.5%, cholic acid 5.0%, glucose 0.5%, $NH_4NO_3$ 0.2%, $KH_2PO_4$ 0.2%, $K_2HPO_4$ 0.5%, $MgSO_4.7H_2O$ 0.02% and yeast extract 0.01%) in a test tube (200 mm×21 mm in diameter) and incubated with shaking at 30° C. for 3 days.

Upon examining products accumulated in each medium G by thin layer chromatography, a microbe which selectively produced 3α,7α-dihydroxy-12-keto-5β-cholanic acid or its salt was found and named Arthrobacter CA-35-M-965-3 strain.

The above mentioned procedure is hereafter referred to as "procedure M". According to the procedure M, a treatment of mutation was carried out by using Arthrobacter CA-35-M-965-3 strain as a parent strain. As the result, three strains which selectively produced 3α,7α-dihydroxy-12-keto-5β-cholanic acid or its salt were found and named Arthrobacter CA-35-A589, Arthrobacter CA-35-A849 and Arthrobacter CA-35-A-1071 strains, respectively.

From the colony of Arthrobacter CA-35-A589 strain, two superior strains were isolated and these strains were named Arthrobacter CA-35-A589-29-32 strain and Arthrobacter CA-35-A589-47 strain, respectively. One superior strain was also isolated from the colony of Arthrobacter CA-35-A-1071 strain and named Arthrobacter CA-35-A-1071-15 -strain.

Further one superior strain was produced by using Arthrobacter CA-35-A849 strain was a parent strain according to the procedure M and named Arthrobacter CA-35-A-1448 strain. Arthrobacter Ca-35-A-1475 strain was produced by using Arthrobacter CA-35-A-1448 strain as a parent strain according to the procedure M. Arthrobacter CA-35-A-1766 strain was produced by using Arthrobacter CA-35-A-1071 strain as a parent strain according to the procedure M, and Arthrobacter CA-35-A-1766-15 strain was isolated from the colony of the resulting Arthrobacter CA-35-A-1766 strain.

Arthrobacter CA-35-Y-37-12 strain was produced according to the following procedure.

One loopful of Arthrobacter CA-35 strain (FERM-P No. 5145; ATCC No. 31651) cultivated on a slant of medium A was inoculated into medium B (10 ml) in a test tube (200 mm×21 mm in diameter) and incubated with shaking at 30° C. for 20 hours. Microbial cells were harvested by centrifuging (10,000 r.p.m.) at 5° C. for 5 minutes under aseptic conditions. The cells were suspended in a sterilized water (10 ml). The suspension was put into a Petri dish (diameter 7.5 cm) placed at about 27 cm distant under a 15 W ultraviolet lamp (2537 Å) in a germ-free box and irradiated with ultraviolet rays for 10 minutes. Under this condition, a lethal rate of Arthrobacter CA-35 strain was about 99.9%.

After irradiation, the microbial cells were harvested by a membrane filter, washed with 0.1 M phosphate buffer and suspended in the same buffer. The resulting suspension was diluted with a normal saline solution and the above cultivation using media D to G was repeated to obtain a superior strain which selectively produced 3α,7α-dihydroxy-12-keto-5β-cholanic acid or its salt.

EXAMPLE 1

Arthrobacter CA-35 strain (FERM-P No. 5145; ATCC No. 31651) was cultivated as follows:

| Composition of culture medium | |
|---|---|
| Cholic acid | 100 g |
| Ammonium nitrate | 2.0 g |
| Potassium dihydrogen phosphate | 2.0 g |
| Dipotassium hydrogen phosphate | 5.0 g |
| Magesium sulfate heptahydrate | 0.2 g |
| Yeast extract | 0.1 g |
| Sodium hydroxide | 10 g |
| Distilled water | to 1 liter |

The above ingredients were admixed to obtain a culture medium (1 liter). Each 100 ml portion of the culture medium was distributed to ten Sakaguchi flasks (volume 500 ml) and autoclaved at 120° C. for 15 minutes. To each flask, there was added 10 ml portion of seed culture which was obtained by previously cultivating the strain in the same medium with shaking at 30° C. for 2 days. Each flask was incubated on a shaker at 30° C. for 2 days.

After completion of cultivation, the culture broth was combined and centrifuged to remove microbial cells. The resulting supernatant was acidified by addition of 1 N aqueous hydrochloric acid (600 ml) to form a precipitate. The precipitate was separated and the remaining solution was extracted with ethyl acetate (1 liter). Ethyl acetate was distilled off from the extract by a rotary evaporator and the residue was combined with the above precipitate to obtain a mixture of cholanic acid derivatives and cholic acid (85 g).

A small portion of the mixture was dissolved in methanol in a concentration of 1%. The solution (10 μl) was injected to a high-speed liquid chromatography apparatus equipped with a μBondapak C-18 column (HLC-GPC-244 type produced by Waters in U.S.A.).

The column was eluted with water-methanol (30:70, v/v, pH 2.5) at the rate of 1 ml/min. and refractive index of the eluate was measured.

The accompanying FIG. 1 shows the resulting chromatogram. The peaks A, B, C and D in FIG. 1 correspond to those of the reference standards of 7α-hydroxy-3,12-diketo-5β-cholanic acid, 3α,7α-dihydroxy-12-keto-5β-cholanic acid, 7α,12α-dihydroxy-3-keto-5β-cholanic acid and cholic acid, respectively.

Figure 2:
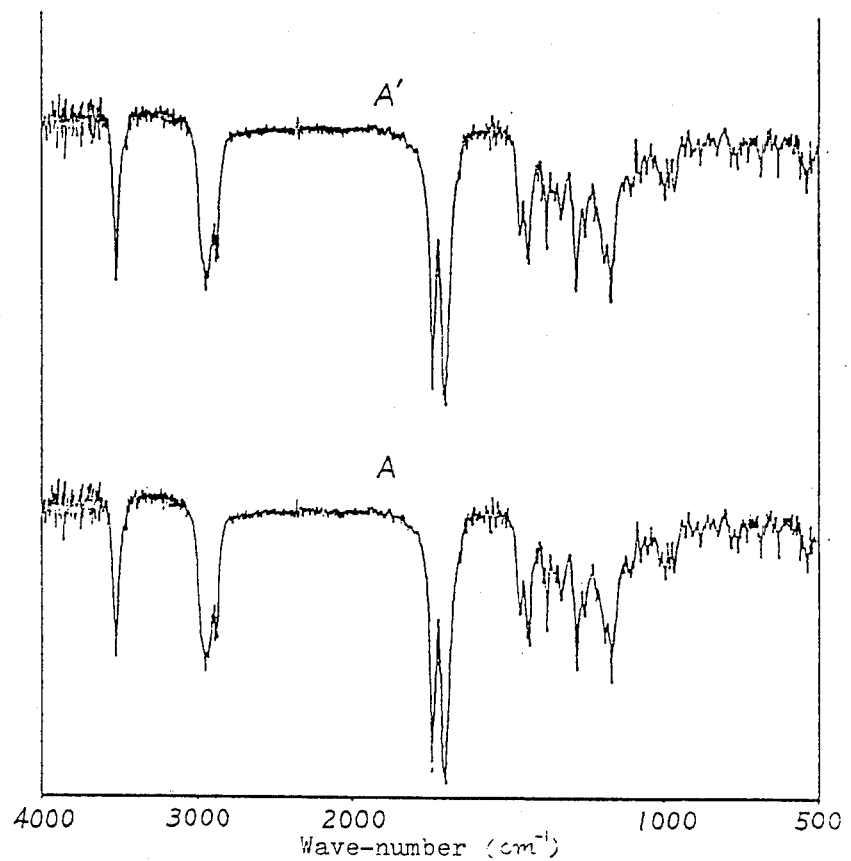
Figure 3:
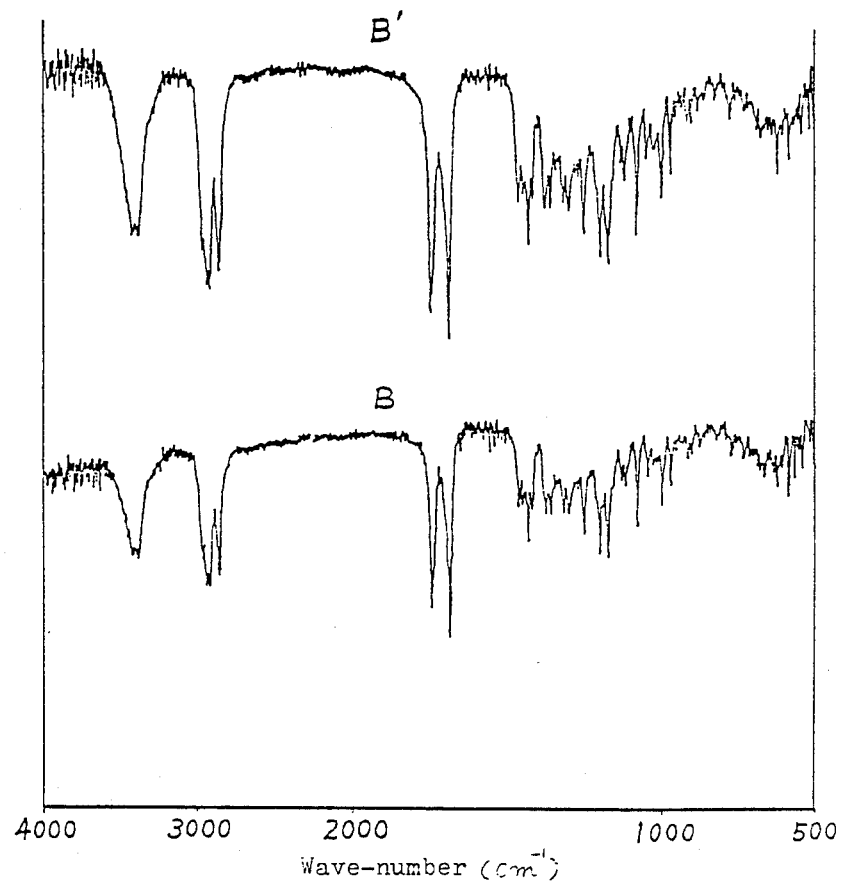
Figure 4:
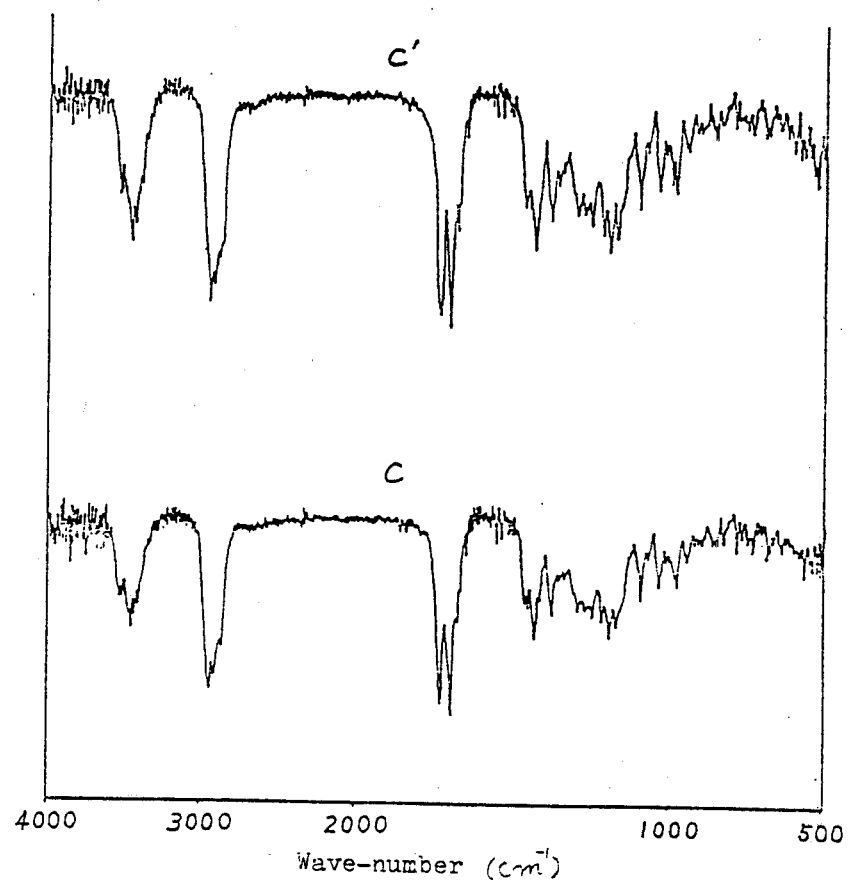

Further, when the compounds in the fractions corresponding to the peaks A, B and C were isolated and their chemical constitutions were determined based on the mass spectra, IR spectra and NMR spectra thereof, these spectra showed that these compounds were 7α-hydroxy-3,12-diketo-5β-cholanic acid, 3α,7α-dihydroxy-12-keto-5β-cholanic acid and 7α,12α-dihydroxy-3-keto-5β-cholanic acid, respectively. The accompanying FIGS. 2, 3 and 4 show the IR spectra (A, B and C) of methyl esters of the compounds corresponding to the peaks A, B and C in comparison with those of the reference standards (A', B' and C'), respectively.

The melting points of the compounds and methyl esters thereof corresponding to the peaks A, B and C are shown in Table 2.

TABLE 2

| Compounds | Melting points of the methyl esters (°C.) | | Melting points of the free acids (°C.) | |
|---|---|---|---|---|
| | Found | Literature | Found | Literature |
| Peak A | 150–152 | 152–154 | — | — |
| Peak B | 154–156 | 156–157 | 219–220 | 221–222 |
| Peak C | 168–169 | 169–172 | 185–186 | 186–188 |

The yield of the products and the amount of cholic acid which remained without being converted were calculated based on the area ratio of the chromatogram of FIG. 1. The results are shown in Table 3.

TABLE 3

| Compounds | Area ratio | Conversion rate (%) | Yield or amount (g) |
|---|---|---|---|
| 7α-hydroxy-3,12-diketo-5β-cholanic acid (peak A) | 28.54 | 28.54 | 24.3 |
| 3α,7α-dihydroxy-12-keto-5β-cholanic acid (peak B) | 63.06 | 63.06 | 53.6 |
| 7α,12α-dihydroxy-3-keto-5β-cholanic acid (peak C) | 1.54 | 1.54 | 1.30 |
| cholic acid (peak D) | 6.86 | 6.86 | 5.80 |

EXAMPLE 2

The same procedure as described in Example 1 was repeated except that the glucose (5.0 g/l) was further added to the medium to obtain a mixture of products and cholic acid which remained without being converted (91.0 g). The mixture (91.0 g) was dissolved in methanol (270 ml) and added thereto conc. hydrochloric acid (9 ml). The resulting solution was heated under reflux for 20 minutes to convert the products and cholic acid into methyl esters thereof.

Silica gel C-200 (1500 g) was packed in a column (1200 mm×70 mm in diameter) and the above methyl esters were adsorbed thereto. The column was eluted with chloroform to obtain 7α-hydroxy-3,12-diketo-5β-cholanic acid methyl ester (25.1 g). Then, the column was eluted with chloroform-ethanol (99:1, v/v) to obtain, firstly, 7α,12α-dihydroxy-3-keto-5β-cholanic acid methyl ester (1.40 g) and then 3α,7α-dihydroxy-12-keto-5β-cholanic acid methyl ester (56.4 g).

These methyl esters were hydrolized to obtain 7α-hydroxy-3,12-diketo-5β-cholanic acid (24.8 g), 7α,12α-dihydroxy-3-keto-5β-cholanic acid (1.38 g) and 3α,7α-dihydroxy-12-keto-5β-cholanic acid (56.0 g).

EXAMPLE 3

The same procedure as described in Example 1 was repeated except that a concentration of cholic acid was varied and sodium hydroxide was added to a medium in an amount of 10% by weight based on cholic acid used. The yield of products and the amount of cholic acid which remained without being converted at each concentration of the substrate (cholic acid) are shown in Table 4.

TABLE 4

| | Yields Substrate concentration (g/l) | | |
|---|---|---|---|
| Compounds | 50 | 200 | 300 |
| 3α,7α-dihydroxy-12-keto-5β-cholanic acid | 27.1 g | 108.3 g | 47.4 g |
| 7α-hydroxy-3,12-diketo-5β-cholanic acid | 12.3 g | 49.0 g | 21.4 g |
| 7α,12α-dihydroxy-3-keto-5β-cholanic acid | 0.7 g | 2.65 g | 1.20 g |
| cholic acid | small amount | 20.1 g | 230 g |

EXAMPLE 4

The same procedure as described in Example 2 was repeated except that each flask was incubated on a shaker at 30° C. for 24 hours to obtain a mixture of products and cholic acid which remained without being converted (98.0 g). The mixture was subjected to high-speed liquid chromatography under the same conditions as in Example 1 to determine the composition thereof. The results are shown in Table 5.

TABLE 5

| Compounds | ratio |
|---|---|
| 3α,7α-dihydroxy-12-keto-5β-cholanic acid | 67.7 |
| 7α-hydroxy-3,12-diketo-5β-cholanic acid | 8.3 |
| 7α,12α-dihydroxy-3-keto-5β-cholanic acid | 4.0 |
| cholic acid | 20.0 |

EXAMPLE 5

The same procedure as described in Example 2 was repeated except that 20 ml portion of seed culture obtained by cultivating at 30° C. for 24 hours was added to each flask to obtain a mixture of products and cholic acid which remained without being converted (117.0 g). The mixture was subjected to high-speed liquid chromatography under the same conditions as in Example 1 to determin the composition thereof. The results are shown in Table 6.

TABLE 6

| Compounds | ratio |
|---|---|
| 3α,7α-dihydroxy-12-keto-5β-cholanic acid | 63.3 |
| 7α-hydroxy-3,12-diketo-5β-cholanic acid | 23.5 |
| 7α,12α-dihydroxy-3-keto-5β-cholanic acid | 2.0 |
| cholic acid | 11.2 |

EXAMPLE 6

Arthrobacter CA-35-A589-29-32 strain (FERM-P No. 5521; ATCC No. 31652) was cultivated as follows:

| Composition of culture medium | |
|---|---|
| Cholic acid | 100 g |
| Ammonium nitrate | 2.0 g |
| Potassium dihydrogen phosphate | 2.0 g |
| Dipotassium hydrogen phosphate | 5.0 g |
| Magnesium sulfate heptahydrate | 0.2 g |
| Yeast extract | 0.1 g |
| Sodium hydroxide | 10 g |
| Glucose | 5.0 g |

-continued

| Composition of culture medium | |
|---|---|
| Tap water | to 1 liter |

The above ingredients other than glucose were admixed in tap water to adjust the volume to 800 ml and autoclaved at 120° C. for 15 minutes. Glucose was dissolved in tap water (200 ml) and autoclaved at 110° C. for 30 minutes. After cooling, both solutions were combined to obtain a culture medium (1 liter). Each 100 ml portion of the culture medium was distributed to ten Sakaguchi flasks (volume 500 ml) under aseptic conditions. To each flask, there was added 2 ml portion of seed culture which was obtained by previously cultivating the strain in the same medium with shaking at 30° C. for 14 hours. Each flask was incubated on a shaker at 30° C. for 3 days.

After completion of cultivation, the culture broth was combined and centrifuged to remove microbial cells. The resulting supernatant was acidified by addition of 1 N aqueous hydrochloric acid (600 ml) to form a precipitate. The precipitate was separated and the residual solution was extracted with ethyl acetate (1 liter). Ethyl acetate was distilled off from the extract by a rotary evaporator and the residue was combined with the above precipitate to obtain a mixture of cholanic acid derivatives and cholic acid (99.3 g).

A small portion of the mixture was dissolved in methanol in a concentration of 2%. The solution (10 μl) was injected to a high-speed liquid chromatography apparatus equipped with a μBondapak C-18 column (HLC-GPC-244 type).

The column was eluted with water-methanol (30:70, v/v, pH 4.0) at the rate of 1 ml/min. and refractive index of the elute was measured.

Figure 5:
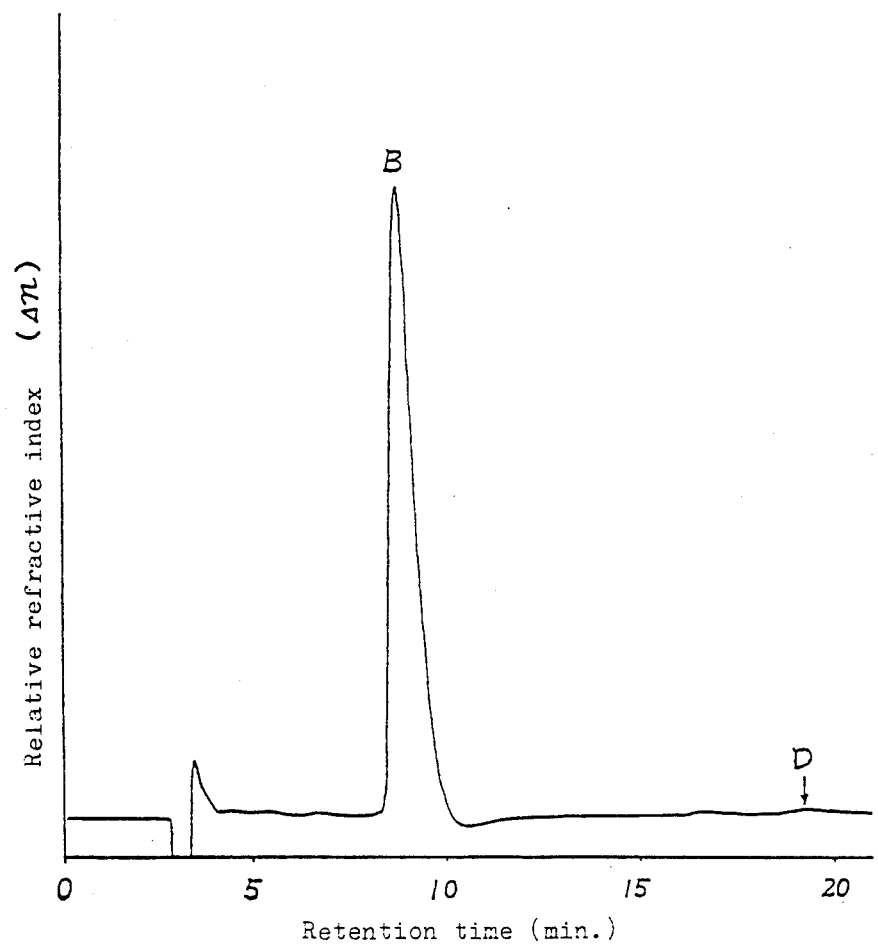

The accompanying FIG. 5 shows the resulting chromatogram. The peaks B and D in FIG. 5 are corresponding to those of the reference standards of 3α,7α-dihydroxy-12-keto-5β-cholanic acid and cholic acid, respectively.

When the compound in the fraction corresponding to the peak B was isolated and its chemical constitution was determined based on the mass spectrum, IR spectrum and NMR spectrum, these spectra showed that the compound was 3α,7α-dihydroxy-12-keto-5β-cholanic acid.

The yield of the products and the amount of cholic acid which remained without being converted were calculated based on the area ratio of the chromatogram of FIG. 5. The results are shown in Table 7.

TABLE 7

| Compounds | Conversion* rate (%) | Yield or amount (g) |
|---|---|---|
| 3α,7α-dihydroxy-12-keto-5β-cholanic acid (peak B) Other derivatives | 98.85 | 98.16 |

TABLE 7-continued

| Compounds | Conversion* rate (%) | Yield or amount (g) |
|---|---|---|
| produced from cholic acid | 0.59 | 0.59 |
| cholic acid (peak D) | 0.56 | 0.55 |

*conversion rate was calculated based on the area ratio.

EXAMPLE 7

The same procedure as described in Example 6 was repeated except that a microbial cells suspension which was prepared by separating microbial cells from the seed culture (10 ml) by centrifugation and suspending them in sterilized water (10 ml) was added to each flask in stead of 2 ml of seed culture to obtain a mixture of products and remaining cholic acid (9.5 g). The mixture (99.5 g) was dissolved in methanol (270 ml) and added thereto conc. hydrochloric acid (9 ml). The resulting solution was heated under reflex for 20 minutes to convert the products and cholic acid into methyl esters thereof.

Silica gel C-200 (1500 g) was packed in a column (1200 mm×70 mm in diameter) and the above methyl esters were adsorbed thereto. The column was eluted with chloroform-ethanol (99:1, v/v) to obtain 3α,7α-dihydroxy-12-keto-5β-cholanic acid methyl ester (102.0 g) which was hydrolyzed to obtain 3α,7α-dihydroxy-12-keto-5β-cholanic acid (98.5 g).

EXAMPLE 8

The same procedure as described in Example 6 was repeated except that the concentration of cholic acid was varied, sodium hydroxide was added to a medium in an amount of 10% by weight based on cholic acid used and 1 N aqueous hydrochloric acid was added in an amount of 60 ml per 1 g of sodium hydroxide used to form a precipitate. The conversion rate or yeild of the product and the amount of remaining cholic acid at each concentration of the substrate (cholic acid) are shown in Table 8.

TABLE 8

| | Conversion rate or yield Substrate concentration (g/l) | | | | | | |
|---|---|---|---|---|---|---|---|
| Compounds | 1 | 5 | 10 | 20 | 50 | 100 | 200 |
| 3α,7α-dihydroxy-12-keto-5β-cholanic acid | 96.7%* | 98.0* | 9.3 g | 19.5 g | 49.6 g | 98.2 g | 129.2 g |
| cholic acid | 0.4% | 0.7%* | 0.1 g | 0.2 g | 0.1 g | 0.6 g | 70.0 g |

*Conversion rate

EXAMPLE 9

The same procedure as described in Example 6 was repeated except that *Arthrobacter CA*-35-A589-47 strain (FERM-P No. 5523; ATCC No. 31653) was used in stead of Arthrobacter CA-35-A589-29-32 strain, the concentrations of cholic acid and sodium hydroxide in the medium were changed to 50 g/l and 5 g/l, respectively and each flask was incubated at 30° C. for 35 hours to obtain a mixture of products and remaining cholic acid (49.31 g).

The mixture was subjected to same high-speed liquid chromatography under the same conditions as in Example 6.

Figure 6:
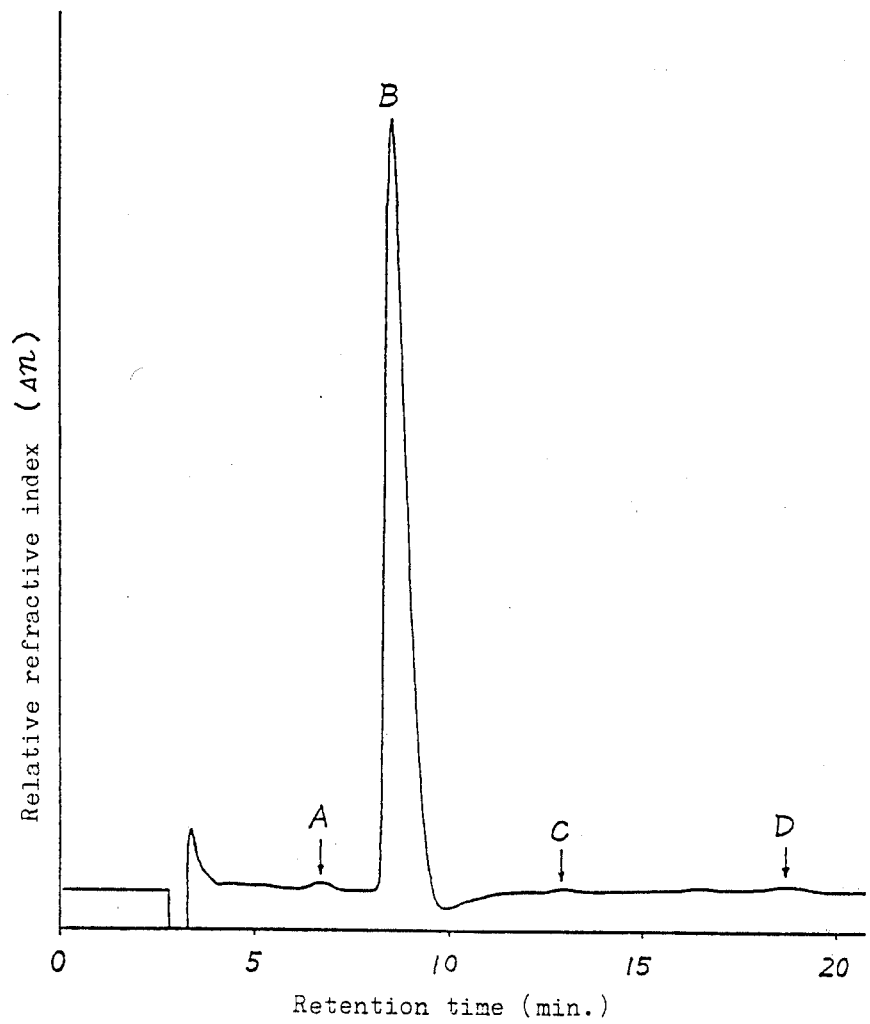

The accompanying FIG. 6 shows the resulting chromatogram. The peaks A, B, C and D in FIG. 6 correspond to those of the reference standards of 7α- hydroxy-3,12-diketo-5β-cholanic acid, 3α,7α-dihydroxy-12-keto-5β-cholanic acid, 7α,12α-dihydroxy-3-keto-5β-cholanic acid and cholic acid, respectively.

When the fractions corresponding to the peaks A, B, C and D were separated and subjected to thin layer chromatography, each fraction corresponding to the peak B, C or D contained a single compound. The fraction corresponding to the peak A was a mixture of 7α-hydroxy-3,12-diketo-5β-cholanic acid and another unidentified material.

The yield of the products and the amount of cholic acid which remained without being converted were calculated based on the area ratio of the chromatogram of FIG. 6. The results are shown in Table 9.

TABLE 9

| Compounds | Conversion rate (%) | Yield or amount (g) |
| --- | --- | --- |
| 7αhydroxy-3,12-diketo-5β-cholanic acid and unidentified material (peak A) | 0.80 | 0.39 |
| 3α,7α-dihydroxy-12-keto-5β-cholanic acid (peak B) | 98.01 | 48.33 |
| 7α,12α-dihydroxy-3-keto-5β-cholanic acid (peak C) | 0.25 | 0.13 |
| other derivatives | 0.24 | 0.12 |
| cholic acid (peak D) | 0.70 | 0.35 |

EXAMPLE 10

The same procedure as described in Example 9 was repeated except that Arthrobacter CA-35-A849 strain (FERM-P No. 5524; ATCC No. 31654) was used in stead of Arthrobacter CA-35-A589-47 strain to obtain a mixture of products and remaining cholic acid (49.34 g).

The mixture was subjected to high-speed liquid chromatography under the same conditions as in Example 6.

Figure 7:
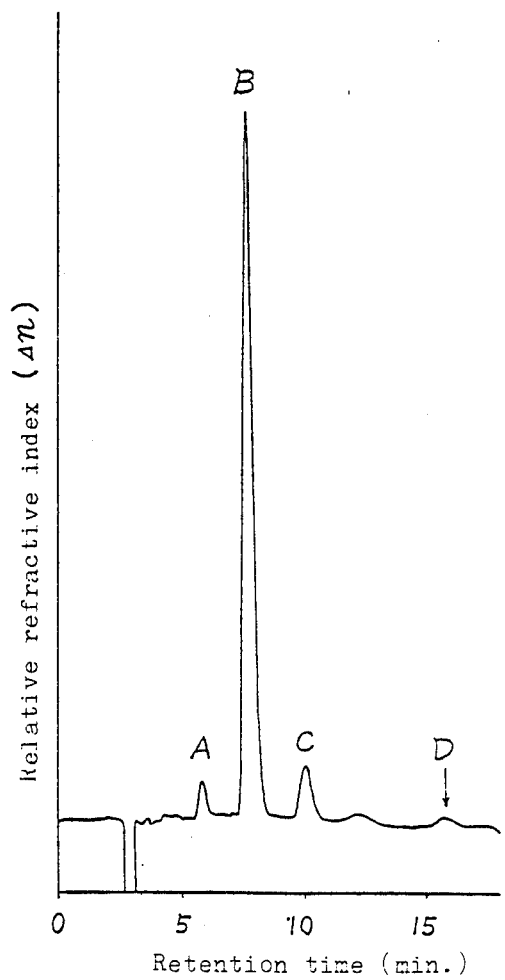

The accompanying FIG. 7 shows the resulting chromatogram. The peaks A, B, C and D in FIG. 7 correspond to those of the reference standards of 7α-hydroxy-3,12-diketo-5β-cholanic acid, 3α,7α-dihydroxy-12-keto-5β-cholanic acid, 7α,12α-dihydroxy-3-keto-5β-cholanic acid and cholic acid, respectively.

When the fractions corresponding to the peaks A, B, C and D were separated and subjected to thin layer chromatography, each fraction contained a single compound.

The yield of the products and the amount of cholic acid which remained without being converted were calculated based on the area ratio of the chromatogram of FIG. 7. The results are shown in Table 10.

TABLE 10

| Compounds | Conversion rate (%) | Yield of amount (g) |
| --- | --- | --- |
| 7α-hydroxy-3,12-diketo-5β-cholanic acid (peak A) | 3.2 | 1.58 |
| 3α,7α-dihydroxy-12-keto-5-cholanic acid (peak B) | 83.5 | 41.20 |
| 7α,12α-dihydroxy-3-keto-5β-cholanic acid (peak C) | 7.9 | 3.90 |
| other derivatives | 2.8 | 1.38 |
| cholic acid (peak D) | 2.6 | 1.28 |

EXAMPLE 11

The same procedure as described in Example 9 was repeated except that Arthrobacter CA-35-A-1071-15 strain (FERM-P No. 5525; ATCC No. 31655) was used in stead of Arthrobacter CA-35-A589-47 strain to obtain a mixture of products and remaining cholic acid (49.31 g).

The mixture was subjected to high-speed liquid chromatography under the same conditions as in Example 6.

Figure 8:
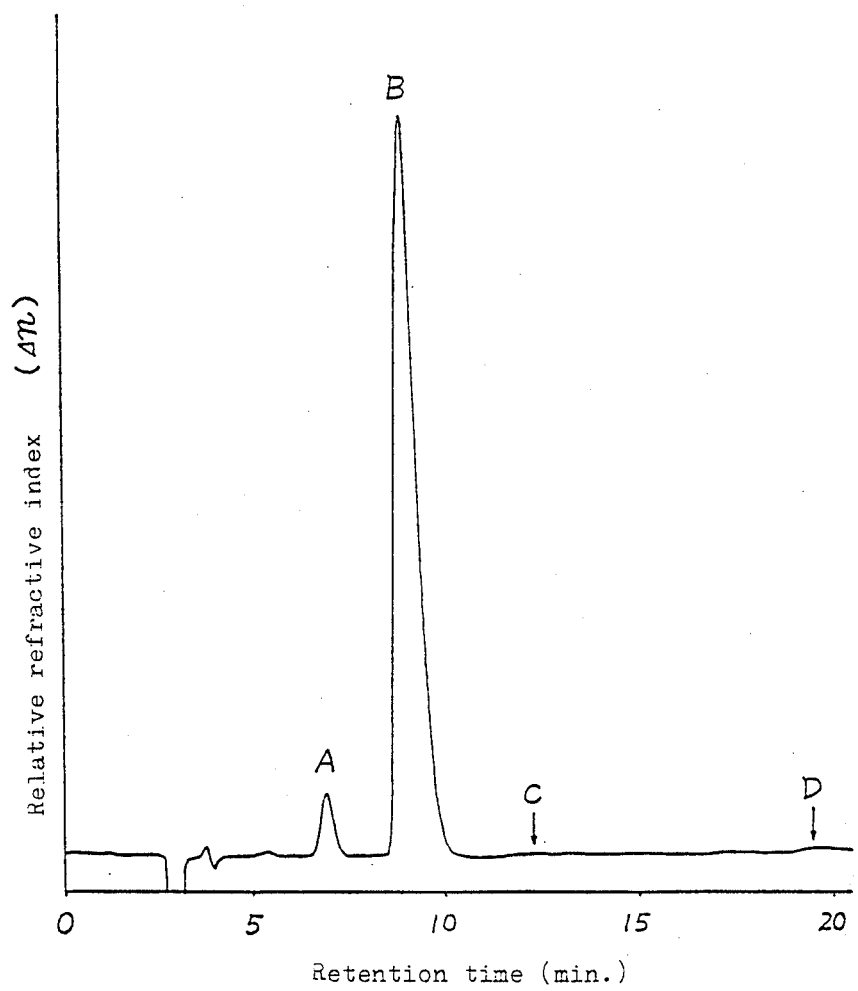

The accompanying FIG. 8 shows the resulting chromatogram. The peaks A, B, C and D in FIG. 8 correspond to those of the reference standards of 7α-hydroxy-3,12-diketo-5β-cholanic acid, 3α,7α-dihydroxy-12-keto-5β-cholanic acid, 7α,12α-dihydroxy-3-keto-5β-cholanic acid and cholic acid, respectively.

When the fractions corresponding to the peaks A, B, C and D were separated and subjected to thin layer chromatography, each fraction corresponding to the peak B, C or D contained a single compound. The fraction corresponding to the peak A was a mixture of 7α-hydroxy-3,12-diketo-5β-cholanic acid and another unidentified material.

The yield of the products and the amount of remaining cholic acid were calculated based on the area ratio of the chromatogram of FIG. 8. The results are shown in Table 11.

TABLE 11

| Compounds | Conversion rate (%) | Yield or amount (g) |
| --- | --- | --- |
| 7α-hydroxy-3,12-diketo-5β-cholanic acid and unidentified material (peak A) | 5.2 | 2.56 |
| 3α,7α-dihydroxy-12-keto-5β-cholanic acid (peak B) | 93.9 | 46.30 |
| 7α,12α-dihydroxy-3-keto-5β-cholanic acid (peak C) | 0.2 | 0.10 |
| other derivatives | 0.2 | 0.10 |
| cholic acid | 0.5 | 0.25 |

EXAMPLE 12

The same procedure as described in Example 9 was repeated except that Arthrobacter CA-35-A-1448 strain (FERM-P No. 5526; ATCC No. 31656) was used in stead of Arthrobacter CA-35-A589-47 strain to obtain a mixture of products and remaining cholic acid (49.30 g).

The mixture was subjected to high-speed liquid chromatography under the same conditions as in Example 6.

Figure 9:
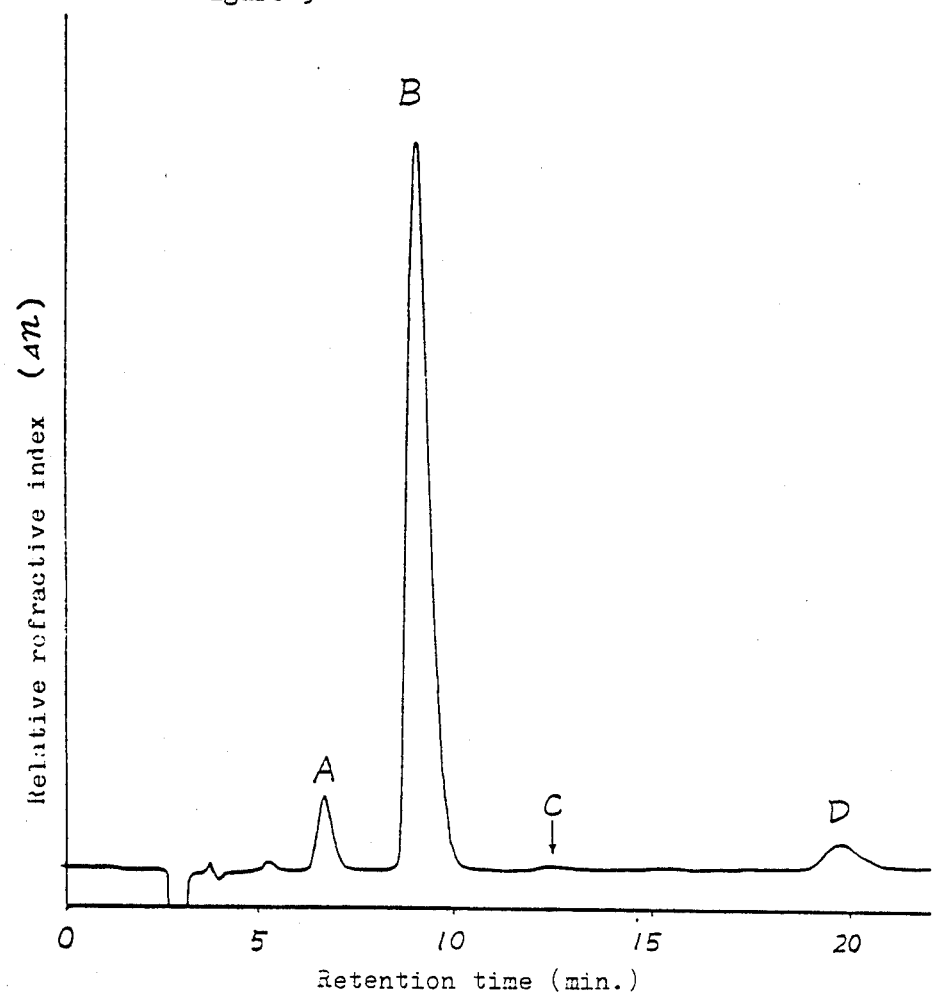

The accompanying FIG. 9 shows the resulting chromatogram. The peaks A, B, C and D in FIG. 9 correspond to those of the reference standards of 7α-hydroxy-3,12-diketo-5β-cholanic acid, 3α,7α-dihydroxy-12-keto-5β-cholanic acid, 7α,12α-dihydroxy-3-keto-5β-cholanic acid and cholic acid, respectively.

When the fractions corresponding to the peaks A, B, C and D were separated and subjected to thin layer chromatography, each fraction corresponding to the peak B, C or D contained a single compound. The fraction corresponding to the peak A was a mixture of 7α-hydroxy-3,12-diketo-5β-cholanic acid and another unidentified material.

The yields of the products and the amount of cholic acid which remained without being converted were calculated based on the area ratio of the chromatogram of FIG. 9. The results are shown in Table 12.

TABLE 12

| Compounds | Conversion rate (%) | Yield or amount (g) |
| --- | --- | --- |
| 7α-hydroxy-3,12-diketo-5β-cholanic acid and unidentified material (peak A) | 6.5 | 3.20 |
| 3α,7α-dihydroxy-12-keto-5β-cholanic acid (peak B) | 88.0 | 43.39 |
| 7α,12α-dihydroxy-3-keto-5β-cholanic acid (peak C) | 0.3 | 0.15 |
| other derivatives | 0.1 | 0.05 |
| cholic acid (peak D) | 5.1 | 2.51 |

EXAMPLE 13

The same procedure as described in Example 9 was repeated except that Arthrobacter CA-35-A-1475 strain (FERM-P No. 5527; ATCC No. 31657) was used instead of Arthrobacter CA-35-A589-47 strain to obtain a mixture of products and cholic acid which remained without being converted (49.35 g).

The mixture was subjected to high-speed liquid chromatography under the same conditions as in Example 6.

Figure 10:
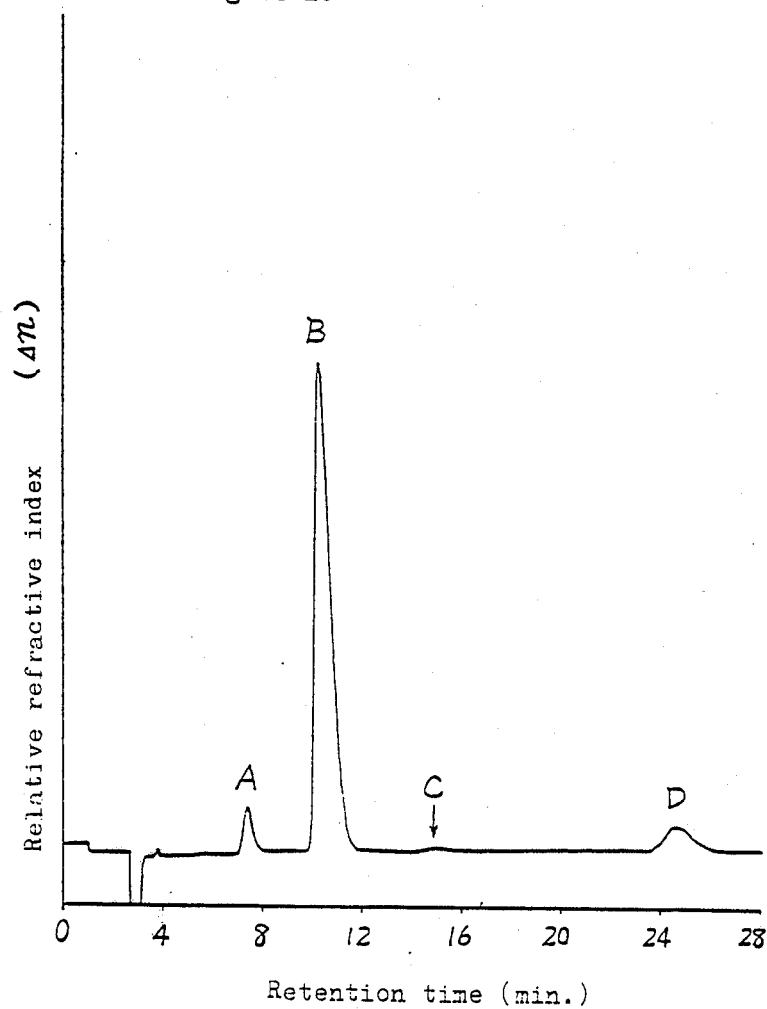

The accompanying FIG. 10 shows the resulting chromatogram. The peaks A, B, C and D in FIG. 10 correspond to those of the reference standards of 7α-hydroxy-3,12-diketo-5β-cholanic acid, 3α,7α-dihydroxy-12-keto-5β-cholanic acid, 7α,12α-dihydroxy-3-keto-5β-cholanic acid and cholic acid, respectively.

When the fractions corresponding to the peaks A, B, C and D were separated and subjected to thin layer chromatography, each fraction contained a single compound.

The yield of the products and the amount of cholic acid were calculated based on the area ratio of the chromatogram of FIG. 10. The results are shown in Table 13.

TABLE 13

| Compounds | Conversion rate (%) | Yield or amount (g) |
| --- | --- | --- |
| 7α-hydroxy-3,12-diketo-5β-cholanic acid (peak A) | 3.26 | 1.61 |
| 3α,7αdihydroxy-12-keto-5β-cholanic acid (peak B) | 92.0 | 45.40 |
| 7α,12α-dihydroxy-3-keto-5β-cholanic acid (peak C) | 0.20 | 0.10 |
| other derivatives | small amount | — |
| cholic acid (peak D) | 4.54 | 2.24 |

EXAMPLE 14

The same procedure as described in Example 9 was repeated except that Arthrobacter CA-35-A-1766-15 strain (FERM-P No. 5528; ATCC No. 31658) was used in stead of Arthrobacter CA-35-A589-47 strain to obtain a mixture of the products and cholic acid (49.27 g).

The mixture was subjected to high-speed liquid chromatography under the same conditions as in Example 6.

Figure 11:
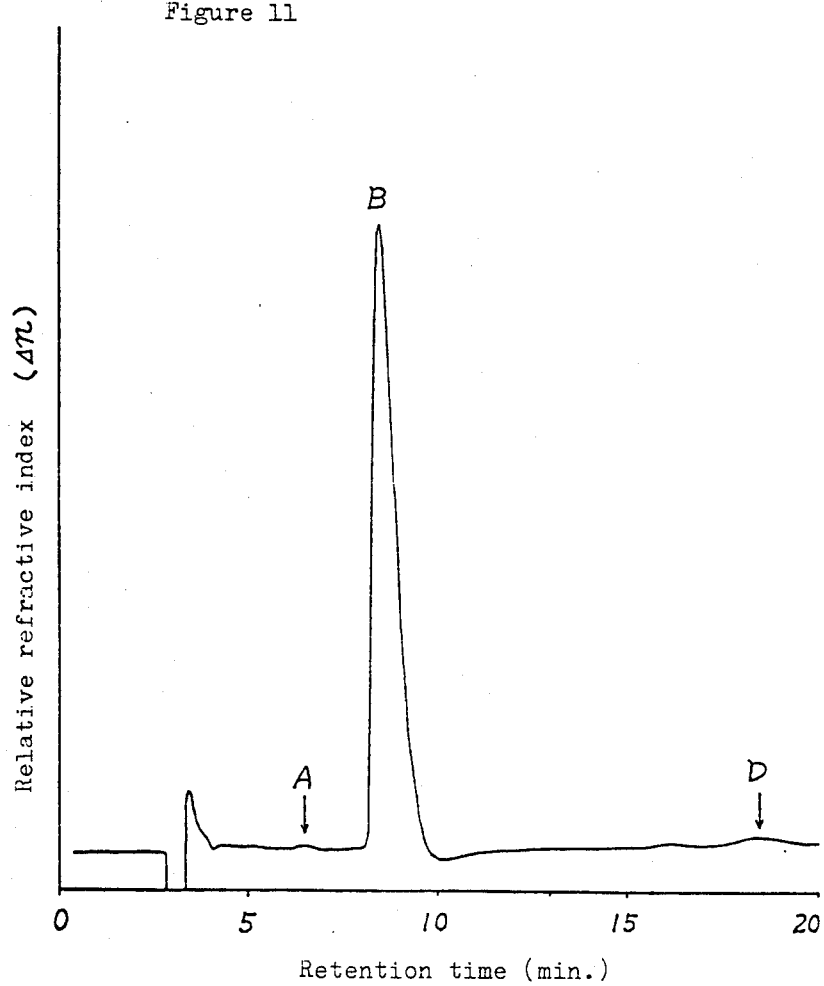

The accompanying FIG. 11 shows the resulting chromatogram. The peaks A, B and D in FIG. 11 correspond to those of the reference standards of 7α-hydroxy-3,12-diketo-5β-cholanic acid, 3α,7α-dihydroxy-12-keto-5β-cholanic acid and cholic acid, respectively.

When the fractions corresponding to the peaks A, B and D were separated and subjected to thin layer chromatography, each fraction contained a single compound.

The yield of the products and the amount of remaining cholic acid were calculated based on the area ratio of the chromatogram of FIG. 11. The results are shown in Table 14.

TABLE 14

| Compounds | Conversion rate (%) | Yield or amount (g) |
| --- | --- | --- |
| 7α-hydroxy-3,12-diketo-5β-cholanic acid (peak A) | 0.23 | 0.11 |
| 3α,7α-dihydroxy-12-keto-5β-cholanic acid (peak B) | 97.02 | 47.80 |
| other derivatives | 0.75 | 0.37 |
| cholic acid (peak D) | 2.0 | 0.99 |

EXAMPLE 15

The same procedure as described in Example 9 was repeated except that Arthrobacter CA-35-M-965-3 strain (FERM-P No. 5529; ATCC No. 31659) was used in stead of Arthrobacter CA-35-A589-47 strain to obtain a mixture of products and cholic acid (49.36 g).

The mixture was subjected to high-speed liquid chromatography under the same conditions as in Example 6.

Figure 12:
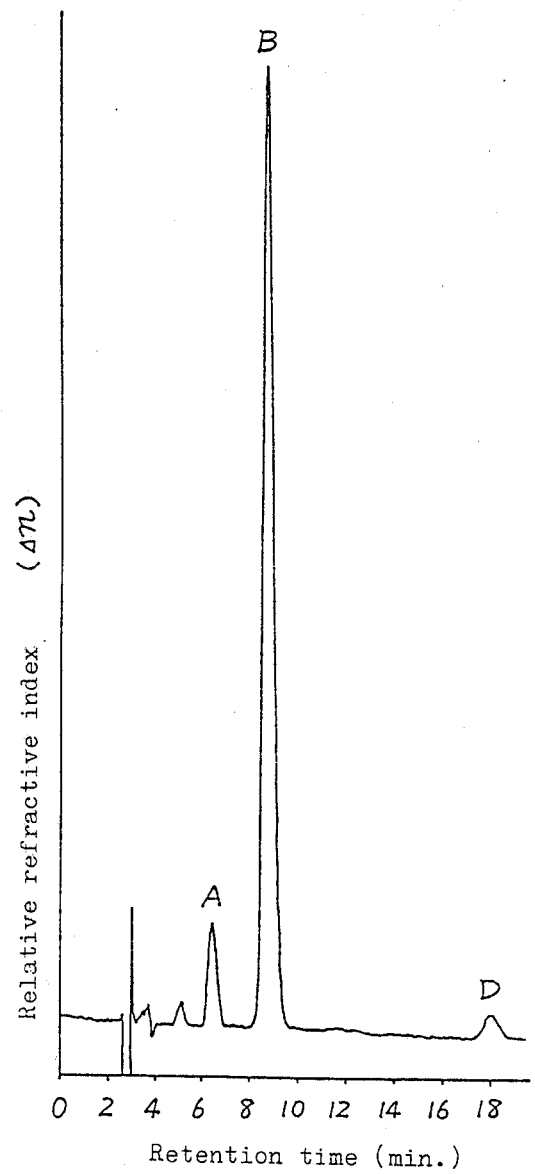

The accompanying FIG. 12 shows the resulting chromatogram. The peaks A, B and D in FIG. 12 correspond to those of the reference standards of 7α-hydroxy-3,12-diketo-5β-cholanic acid, 3α,7α-dihydroxy-12-keto-5β-cholanic acid and cholic acid, respectively.

When the fractions corresponding to the peaks A, B and D were separated and subjected to thin layer chromatography, each fraction corresponding to the peak B or D contained a single compound. The fraction corresponding to the peak A was a mixture of 7α-hydroxy-3,12-diketo-5β-cholanic acid and another unidentified 3,12-diketo-5β-cholanic acid and another unidentified material.

The yield of the products and the amount of remaining cholic acid were calculated based on the area ratio of the chromatogram of FIG. 12. The results are shown in Table 15.

TABLE 15

| Compounds | Conversion rate (%) | Yield or amount (g) |
| --- | --- | --- |
| 7α-hydroxy-3,12-diketo-5β-cholanic acid and unidentified material (peak A) | 8.6 | 4.24 |
| 3α,7α-dihydroxy-12-keto-5β-cholanic acid (peak B) | 85.3 | 42.11 |
| other derivatives | 2.0 | 0.99 |
| cholic acid (peak D) | 4.1 | 2.02 |

EXAMPLE 16

The same procedure as described in Example 9 was repeated except that Arthrobacter CA-35-Y-37-12 strain (FERM-P No. 5530; ATCC No. 31660) was used in stead of Arthrobacter CA-35-A589-47 strain to obtain a mixture of products and cholic acid (49.33 g).

The mixture was subjected to high-speed liquid chromatography under the same conditions as in Example 6.

Figure 13:
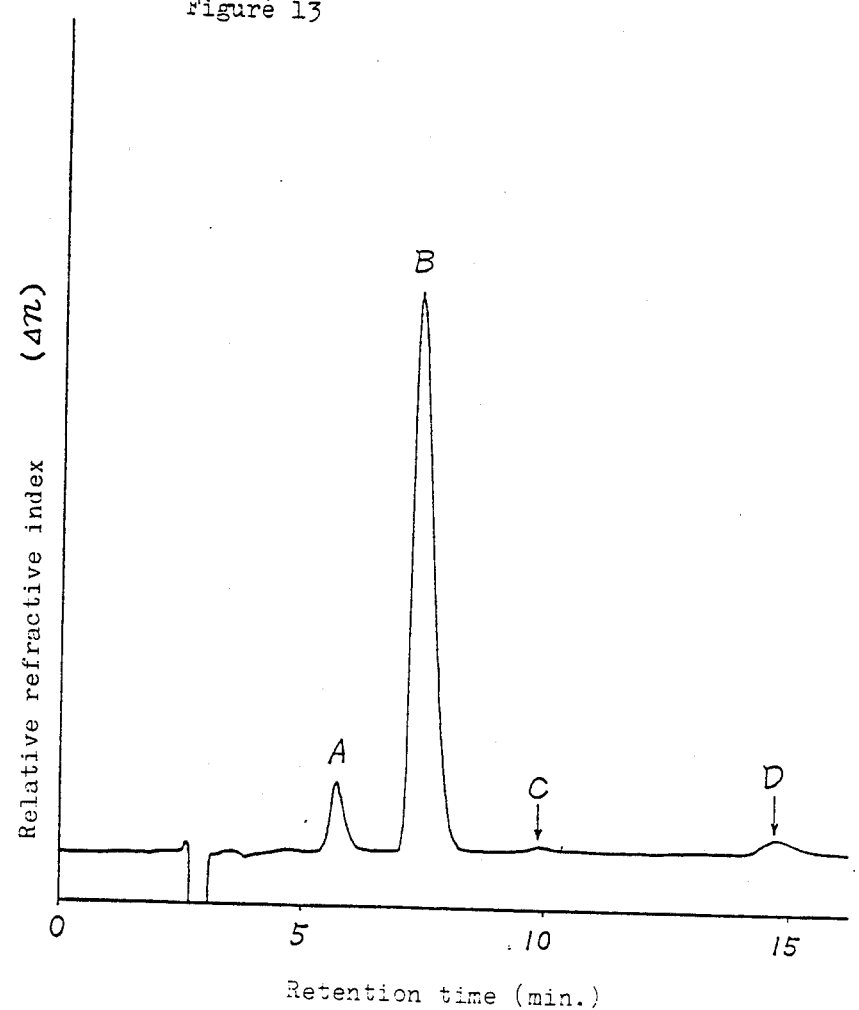

The accompanying FIG. 13 shows the resulting chromatogram. The peaks A, B, C and D in FIG. 13 correspond to those of the reference standards of 7α- hydroxy-3,12-diketo-5β-cholanic acid, 3α,7α-dihydroxy-12-keto-5β-cholanic acid, 7α,12α-dihydroxy-3-keto-5β-cholanic acid and cholic acid, respectively.

When the fractions corresponding to the peaks A, B, C and D were separated and subjected to thin layer chromatography, each fraction contained a single compound.

The yeild of the products and the amount of remaining cholic acid were calculated based on the area ratio of the chromatogram of FIG. 13. The results are shown in Table 16.

TABLE 16

| Compounds | Conversion rate (%) | Yield or amount (g) |
| --- | --- | --- |
| 7α-hydroxy-3,12-diketo-5β-cholanic acid (peak A) | 7.7 | 3.80 |
| 3α,7α-dihydroxy-12-keto-5β-cholanic acid (peak B) | 90.0 | 44.40 |
| 7α,12α-dihydroxy-3-keto-5β-cholanic acid (peak C) | 0.3 | 0.15 |
| cholic acid (peak D) | 2.0 | 0.98 |

EXAMPLE 17

The same procedure as described in Example 1 was repeated except that Brevibacterium CA-6 strain (FERM-P No. 5144; ATCC No 31661) was used instead of Arthrobacter CA-35 strain.

The resulting mixture of products and remaining cholic acid was subjected to high-speed liquid chromatography as in Example 1.

Figure 14:
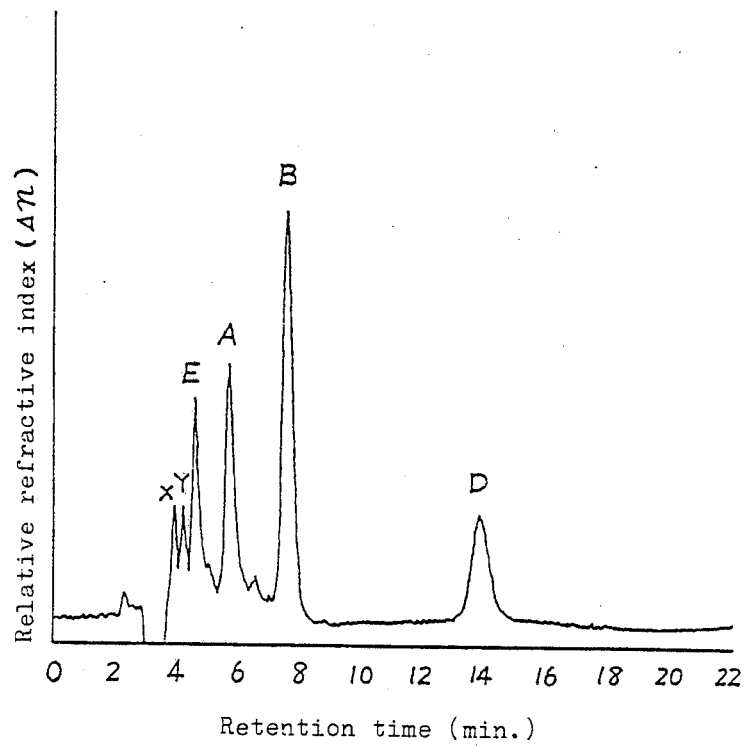

The accompanying FIG. 14 shows the resulting chromatogram.

When the compounds in the fractions corresponding to the peaks E, A, B and D were isolated and their chemical constitutions were determined based on the mass spectra, IR spectra and NMR spectra thereof, these spectra showed that these compounds were 7α-hydroxy-3,12-diketo-Δ$^4$-cholenic acid, 7α-hydroxy-3,12-diketo-5β-cholanic acid, 3α,7α-dihydroxy-12-keto-5β-cholanic acid and cholic acid, respectively. The compounds in the fractions corresponding to the peaks X and Y were unidentified.

In the chromatogram of FIG. 14, the area ratio of the peaks other than peaks X and Y (i.e. the area ratio E:A:B:D) is 12.2:22.2:44.9:20.7.

EXAMPLE 18

The same procedure as described in Example 1 was repeated except that Corynebacterium CA-53 strain (FERM-P No. 5532; ATCC No. 31662) was used instead of Arthrobacter CA-35 strain to obtain a mixture of products and cholic acid (82 g).

The resulting mixture was subject to high-speed liquid chromatography under the same conditions as in Example 1 except that water-methanol (30:70, v/v, pH 4.0) was used, in stead of water-methanol (30:70, v/v, pH 2.5) as an eluate.

The accompanying FIG. 15 shows the resulting chromatogram. The peaks A, B, C and D in FIG. 15 correspond to those of the reference standards of 7α-hydroxy-3,12-diketo-5β-cholanic acid, 3α,7α-dihydroxy-12-keto-5β-cholanic acid, 7α-hydrolxy-3,12-diketo-Δ$^4$-cholenic acid and cholic acid, respectively.

When the compounds in the fractions corresponding to the peaks A, B and C were isolated and their chemical constitutions were determined based on the mass spectra, IR spectra and NMR spectra thereof, these spectra showed that these compounds were 7α-hydroxy-3,12-diketo-5β-cholanic acid, 3α,7α-dihydroxy-12-keto-5β-cholanic acid and 7α-hydroxy-3,12-diketo-Δ$^4$-cholenic acid, respectively.

REFERENCE EXAMPLE 1

3α,7α-dihydroxy-12-keto-5β-cholanic acid (10 g) thus obtained was placed in a three-necked (round bottom) flask and slowly added thereto ethylene glycol (100 ml) and aqueous potassium hydroxide solution (potassium hydroxide 10 g + water 20 ml). Further, 85% hydrazine hydrate (10 ml) was added and then, the resulting mixture was fluxed at 100° C. for 2 hours. The temperature was gradually elevated and the reflux was continued at 185° to 190° C. for 4 hours to distill off hydrazine hydrate. After cooling, the reaction mixture was diluted with excess water and adjusted to pH 3 to form a precipitate. The precipitate was collected by filtration, washed with water and air-dried to obtain 3α,7α-dihydroxy-5β-cholanic acid (CDCA), yield 8.5 g.

REFERENCE EXAMPLE 2

In a three-necked (round bottom) flask, 7α-hydroxy-3,12-diketo-5β-cholanic acid (3 g) obtained in the above examples was dissolved in pyridine (70 ml) and added thereto tosyl chloride (1 mol). The resulting mixture was reacted at 0° C. for 1 hour and then, refluxed for 5 hours. After reflux, 3 N aqueous hydrochloric acid was added and the reaction mixture was extracted with ether (100 ml). Ether was distilled off from the extract under a reduced pressure to give Δ$^6$- and/or Δ$^7$-3,12-diketo-cholenic acid (2.5 g). The resultant (2 g) was dissolved in 1 N aqueous sodium hydroxide (10 ml) and added thereto Raney nickel (0.1 g). After addition of hydrogen (0.01 mol), the mixture was reacted overnight to obtain 3α,12α-dihydroxy-5β-cholanic acid (deoxycholic acid) and 3α,12α-dihydroxy-5β-cholanic acid (yield: 90%).

What is claimed is:

1. A microbial process for producing a cholanic acid derivative of the formula:

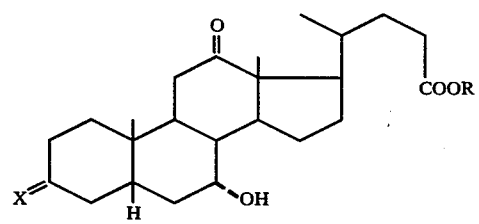

wherein X is

or =O; and R is hydrogen, an alkali metal or an alkaline earth metal, which comprises cultivating a microbe which is capable of growing in a medium containing cholic acid or salt thereof as a substrate to produce the cholanic acid deriviatice and is selected from the group consisting of *Arthrobacter* sp., *Brevibacterium* sp. and *Corynebacterium* sp., in a culture medium containing the substrate and collecting the resulting derivative.

2. A microbial process according to claim 1, wherein the microbe is a member selected from the group consisting of Arthrobacter CA-35 strain (FERM-P No. 5145; ATCC No. 31651), Arthrobacter CA-35-A589-29-32 strain (FERM-P No. 5522; ATCC No. 31652), Arthrobacter CA-35-A589-47 strain (FERM-P No 5523; ATCC No. 31653); Arthrobacter CA-35-A849 strain (FERM-P No. 5524; ATCC No. 31654), Arthrobacter CA-35-A-1071-15 strain (FERM-P No. 5525; ATCC No. 31655), Arthrobacter CA-35-A-1448 strain (FERM-P No. 5526; ATCC No. 31656), Arthrobacter CA-35-A-1475 strain (FERM-P No. 5527; ATCC No. 31657), Arthrobacter CA-35-A-1766-15 strain (FERM-P No. 5288; ATCC No. 31658), Arthrobacter CA-35-M-965-3 strain (FERM-P No. 5529; ATCC No. B 31659), Arthrobacter CA-35-Y-37-12 strain (FERM-P No. 5530; ATCC No. 31660), Brevibacterium CA-6 strain (FERM-P No. 5144; ATCC No. 31661), and Corynebacterium CA-53 strain (FERM-P No. 5532; ATCC No. 31662).

3. A microbial process according to claim 1, wherein the cholanic acid derivatives produced is $3\alpha,7\alpha$-dihydroxy-12-keto-$5\beta$-cholanic acid.

4. A microbial process according to claim 3, wherein the microbe is a member selected from the group consisting of Arthrobacter CA-35-A589-29-32 strain (FERM-P No. 5522; ATCC No. 31652), Arthrobacter CA-35-A589-47 strain (FERM-P No. 5523; ATCC No. 31653), Arthrobacter CA-35-A849 strain (FERM-P No. 5524; ATCC No. 31654), Arthrobacter CA-35-A-1071-15 strain (FERM-P No. 5525; ATCC No. 31655), Arthrobacter CA-35-A-1448 strain (FERM-P No. 5526; ATCC No. 31656), Arthrobacter CA-35-A-1475 strain (FERM-P No. 5527; ATCC No. 31657), Arthrobacter CA-35-A-1766-15 strain (FERM-P No. 5528; ATCC No. 31658), Arthrobacter CA-35-M-965-3 strain (FERM-P No. 5529; ATCC No. 31659), Arthrobacter CA-35-Y-37-12 strain (FERM-P No. 5530; ATCC No. 31660).

5. A microbial process according to claim 1, wherein the substrate is used in a concentration of 1 to 500 g/l as cholic acid.

6. A microbial process according to claim 5, wherein the substrate is used in a concentration of 5 to 300 g/l as cholic acid.

7. A microbial process according to claim 6, wherein the substrate is used in a concentration of 10 to 200 g/l as cholic acid.

8. The process of claim 1 wherein the microbe is of Arthobacter sp.

9. The process of claim 1 wherein the microbe is of Brevibacterium sp.

10. The process of claim 1 wherein the microbe is of Corynebacterium sp.

* * * * *